United States Patent
Jaitzig et al.

(10) Patent No.: US 10,717,998 B2
(45) Date of Patent: Jul. 21, 2020

(54) RECOMBINANT MICROORGANISM FOR IMPROVED PRODUCTION OF FINE CHEMICALS

(71) Applicant: BASF SE, Ludwigshafen (DE)

(72) Inventors: Jennifer Jaitzig, New York, NY (US); Mukesh Kumar, White Plains, NY (US); Shakir Ratani, Elmsford, NY (US); Matthew Blankschien, Dobbs Ferry, NY (US); Qingzhao Wang, Ardsley, NY (US)

(*) Notice: Subject to any disclaimer, the term of this patent is extended or adjusted under 35 U.S.C. 154(b) by 0 days.

(21) Appl. No.: 15/559,323

(22) PCT Filed: Mar. 15, 2016

(86) PCT No.: PCT/EP2016/055582
§ 371 (c)(1),
(2) Date: Sep. 18, 2017

(87) PCT Pub. No.: WO2016/146633
PCT Pub. Date: Sep. 22, 2016

(65) Prior Publication Data
US 2018/0112242 A1    Apr. 26, 2018

Related U.S. Application Data

(60) Provisional application No. 62/134,607, filed on Mar. 18, 2015, provisional application No. 62/134,608, filed on Mar. 18, 2015, provisional application No. 62/134,610, filed on Mar. 18, 2015, provisional application No. 62/134,611, filed on Mar. 18, 2015.

(51) Int. Cl.
| | |
|---|---|
| *C12P 13/06* | (2006.01) |
| *C07K 14/245* | (2006.01) |
| *C12P 7/46* | (2006.01) |
| *C12N 9/00* | (2006.01) |
| *C12P 13/08* | (2006.01) |
| *C12N 9/10* | (2006.01) |
| *C12P 7/40* | (2006.01) |
| *C12P 13/20* | (2006.01) |
| *C12N 15/52* | (2006.01) |
| *C12P 7/56* | (2006.01) |
| *C12N 9/06* | (2006.01) |
| *C12N 9/04* | (2006.01) |
| *C12N 9/02* | (2006.01) |
| *C12N 9/88* | (2006.01) |

(52) U.S. Cl.
CPC ............ *C12P 13/06* (2013.01); *C07K 14/245* (2013.01); *C12N 9/0006* (2013.01); *C12N 9/0008* (2013.01); *C12N 9/0014* (2013.01); *C12N 9/1014* (2013.01); *C12N 9/1029* (2013.01); *C12N 9/88* (2013.01); *C12N 15/52* (2013.01); *C12P 7/40* (2013.01); *C12P 7/46* (2013.01); *C12P 7/56* (2013.01); *C12P 13/08* (2013.01); *C12P 13/20* (2013.01); *C12Y 101/01027* (2013.01); *C12Y 102/01003* (2013.01); *C12Y 203/01008* (2013.01); *C12Y 203/01054* (2013.01); *C12Y 402/01024* (2013.01)

(58) Field of Classification Search
None
See application file for complete search history.

(56) References Cited

U.S. PATENT DOCUMENTS

| | | |
|---|---|---|
| 5,565,350 A | 10/1996 | Kmiec |
| 5,786,313 A | 7/1998 | Schneider et al. |
| 2015/0376663 A1 | 12/2015 | Schroeder et al. |
| 2016/0355829 A1 | 12/2016 | Schroder et al. |
| 2017/0051323 A1 | 2/2017 | Ochrombel et al. |
| 2017/0051324 A1* | 2/2017 | Ochrombel ............ C07K 14/34 |
| 2017/0211106 A1 | 7/2017 | Schroder et al. |

FOREIGN PATENT DOCUMENTS

| | | | |
|---|---|---|---|
| RU | 2355759 C1 | 5/2009 | |
| WO | WO-9429421 A1 | 12/1994 | |
| WO | WO-0015815 A1 | 3/2000 | |
| WO | WO-2007120198 A2 | 10/2007 | |
| WO | WO-2008101857 A2 | 8/2008 | |
| WO | WO-2008119009 A2 | 10/2008 | |
| WO | WO 2009/043803 * | 4/2009 | ............. C12P 13/12 |
| WO | WO-2012150155 A1 | 11/2012 | |
| WO | WO-2012172822 A1 | 12/2012 | |
| WO | WO-2013001055 A1 | 1/2013 | |
| WO | WO-2014087184 A1 | 6/2014 | |
| WO | WO-2015044818 A1 | 4/2015 | |
| WO | WO-2015087226 A1 | 6/2015 | |
| WO | WO-2015/165740 A2 | 11/2015 | |
| WO | WO-2015165746 A1 | 11/2015 | |

OTHER PUBLICATIONS

Zhang et al., "Production of L-alanine by metabolically engineered *Escherichia coli*", Appl Microbiol Biotechnol (2007) 77:355-366. DOI 10.1007/s00253-007-1170-y.*
International Search Report for PCT/EP2016/055582 dated Jun. 15, 2016.
Written Opinion of the International Searching Authority for PCT/EP2016/055582 dated Jun. 15, 2016.
U.S. Appl. No. 61/881,964, Wang.
U.S. Appl. No. 61/881,966, Wang.
U.S. Appl. No. 61/881,968, Wang.
U.S. Appl. No. 61/881,967, Wang.
U.S. Appl. No. 61/881,970, Wang.
U.S. Appl. No. 61/881,972, Wang.
U.S. Appl. No. 61/881,973, Wang.
U.S. Appl. No. 61/881,976, Wang.

(Continued)

*Primary Examiner* — Suzanne M Noakes
(74) *Attorney, Agent, or Firm* — Faegre Drinker Biddle & Reath LLP

(57) ABSTRACT

The present invention relates to a recombinant microorganism, to a method for producing alanine and to the use of the recombinant microorganism for the fermentative production of alanine.

25 Claims, No Drawings
Specification includes a Sequence Listing.

(56) References Cited

OTHER PUBLICATIONS

U.S. Appl. No. 61/881,978, Wang.
U.S. Appl. No. 61/881,975, Wang.
U.S. Appl. No. 61/881,979, Wang.
U.S. Appl. No. 61/881,981, Wang.
U.S. Appl. No. 61/881,980, Wang.
U.S. Appl. No. 61/881,982, Wang.
U.S. Appl. No. 61/881,985, Wang.
U.S. Appl. No. 61/881,987, Wang.
U.S. Appl. No. 61/881,988, Wang.
U.S. Appl. No. 61/881,989, Wang.
U.S. Appl. No. 61/881,991, Wang.
U.S. Appl. No. 61/881,994, Wang.
U.S. Appl. No. 61/881,996, Wang.
U.S. Appl. No. 61/881,983, Wang.
U.S. Appl. No. 61/881,986, Wang.
U.S. Appl. No. 61/881,999, Wang.
U.S. Appl. No. 61/882,001, Wang.
U.S. Appl. No. 61/882,003, Wang.
U.S. Appl. No. 61/882,005, Wang.
U.S. Appl. No. 61/882,006, Wang.
U.S. Appl. No. 61/882,007, Wang.
U.S. Appl. No. 61/915,513, Wang.
U.S. Appl. No. 61/915,516, Wang.
U.S. Appl. No. 61/915,517, Wang.
U.S. Appl. No. 61/195,525, Wang.
U.S. Appl. No. 61/915,527, Wang.
U.S. Appl. No. 61/915,528, Wang.
U.S. Appl. No. 61/915,531, Wang.
U.S. Appl. No. 61/915,532, Wang.
U.S. Appl. No. 61/915,534, Wang.
U.S. Appl. No. 61/915,535, Wang.
U.S. Appl. No. 62/134,607, Wang.
U.S. Appl. No. 62/134,610, Wang.
U.S. Appl. No. 62/134,611, Wang.
Okamura-Ikeda, et al., "Cloning and Nucleotide Sequence of the gcv Operon Encoding the *Escherichia coli* Glycine-Cleavage System", European Journal of Biochemistry, vol. 216, pp. 539-548, 1993.
Hermann, "Industrial Production of Amino Acids by Coryneform Bacteria", Journal of Biotechnology, vol. 104, Issues 1-3, Sep. 4, 2003, pp. 155-172.
Zhang, et al., "Metabolic Evolution of Energy-conserving Pathways for Succinate Production in *Escherichia coli*", Proceedings of the National Academy of Sciences of the United States of American, vol. 106, Issue 48, 2009, pp. 20180-20185.
Pakula, et al., "Genetic analysis of protein stability and function", Annual Review of Genetics, vol. 23, 1989, pp. 289-310.

\* cited by examiner

SEQUENCE LISTING

<160> NUMBER OF SEQ ID NOS: 56

<210> SEQ ID NO 1
<211> LENGTH: 1425
<212> TYPE: DNA
<213> ORGANISM: E.coli

<400> SEQUENCE: 1

```
atgagtactg aaatcaaaac tcaggtcgtg gtacttgggg caggcccgc aggttactcc      60 gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
ggggctaaca ccctggaagt tgaaggtgag aacggtaaaa ccgtgatcaa cttcgacaac     420
gcgatcattg cagcgggttc tcgcccgatc caactgccgt ttattccgca tgaagatccg     480
```

```
cgtatctggg actccactga cgcgctggaa ctgaaagaag taccagaacg cctgctggta    540
atgggtggcg gtatcatcgg tctggaaatg ggcaccgtat accacgcgct gggttcacag    600
attgacgtgg ttgaaatgtt cgaccaggtt atcccggcag ctgacaaaga catcgttaaa    660
gtcttcacca gcgtatcag caagaaattc aacctgatgc tggaaaccaa agttaccgcc    720
gttgaagcga agaagacgg tatttatgtg acgatggaag gcaaaaaagc acccgctgaa    780
ccgcagcgtt acgacgccgt gctggtagcg attggtcgtg tgccgaacgg taaaaacctc    840
gacgcaggca agctggcgt ggaagtggac gaccgtggtt tcatccgcgt tgacaaacag    900
ctgcgtacca acgtaccgca catctttgct atcggcgata cgtcggtca gccgatgctg    960
gcacacaaag gtgttcacga aggtcacgtt gccgctgaag ttatcgccgg taagaaacac   1020
tacttcgatc cgaaagttat cccgtccatc gcctataccg aaccagaagt tgcatgggta   1080
ggtctgactg agaaagaagc gaaagagaaa ggcatcagct atgaaaccgc caccttcccg   1140
tgggctgctt ctggtcgtgc tatcgcttcc gactgcgcag acggtatgac caagctgatt   1200
ttcgacaaag aatctcaccg tgtgatcggt ggtgcgattg tcggtaccaa cggcggcgag   1260
ctgctgggtg aaatcggcct ggcaatcgaa atgggttgtg atgctgaaga catcgcactg   1320
accatccacg cgcacccgac tctgcacgag tctgtgggcc tggcggcaga agtgttcgaa   1380
ggtagcatta ccgacctgcc gaacccgaaa gcgaagaaga gtaa                    1425
```

<210> SEQ ID NO 2
<211> LENGTH: 474
<212> TYPE: PRT
<213> ORGANISM: E.coli

<400> SEQUENCE: 2

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

```
Gln Val Ile Pro Ala Ala Asp Lys Asp Ile Val Lys Val Phe Thr Lys
210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
            245                 250                 255
Ala Pro Ala Glu Pro Gln Arg Tyr Asp Ala Val Leu Val Ala Ile Gly
            260                 265                 270
Arg Val Pro Asn Gly Lys Asn Leu Asp Ala Gly Lys Ala Gly Val Glu
            275                 280                 285
Val Asp Asp Arg Gly Phe Ile Arg Val Asp Lys Gln Leu Arg Thr Asn
290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
            325                 330                 335
Gly Lys Lys His Tyr Phe Asp Pro Lys Val Ile Pro Ser Ile Ala Tyr
            340                 345                 350
Thr Glu Pro Glu Val Ala Trp Val Gly Leu Thr Glu Lys Glu Ala Lys
            355                 360                 365
Glu Lys Gly Ile Ser Tyr Glu Thr Ala Thr Phe Pro Trp Ala Ala Ser
370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
            405                 410                 415
Asn Gly Gly Glu Leu Leu Gly Glu Ile Gly Leu Ala Ile Glu Met Gly
            420                 425                 430
Cys Asp Ala Glu Asp Ile Ala Leu Thr Ile His Ala His Pro Thr Leu
            435                 440                 445
His Glu Ser Val Gly Leu Ala Ala Glu Val Phe Glu Gly Ser Ile Thr
    450                 455                 460
Asp Leu Pro Asn Pro Lys Ala Lys Lys Lys
465                 470

<210> SEQ ID NO 3
<211> LENGTH: 1425
<212> TYPE: DNA
<213> ORGANISM: E.coli

<400> SEQUENCE: 3
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta agcactgct gcacgtagca      180 aaagttatcg aagaagccaa agcgctgcct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
ggggctaaca ccctggaagt tgaaggtgag aacggtaaaa ccgtgatcaa cttcgacaac     420
gcgatcattg cagcgggttc tcgcccgatc caactgccgt ttattccgca tgaagatccg     480
cgtatctggg actccactga cgcgctgaa ctgaaagaag taccagaacg cctgctggta     540
atgggtggcg gtatcatcgg tctggaaatg ggcaccgtat accacgcgct gggttcacag     600
```

```
attgacgtgg ttgaaatgtt cgaccaggtt atcccggcag ctgacaaaga catcgttaaa    660
gtcttcacca agcgtatcag caagaaattc aacctgatgc tggaaaccaa agttaccgcc    720
gttgaagcga agaagacgg tatttatgtg acgatggaag gcaaaaaagc accgctgaa      780
ccgcagcgtt acgacgccgt gctggtagcg attggtcgtg tgccgaacgg taaaaacctc    840
gacgcaggca agctggcgt ggaagtggac gaccgtggtt tcatccgcgt tgacaaacag     900
ctgcgtacca acgtaccgca catctttgct atcggcgata cgtcggtca gccgatgctg     960
gcacacaaag gtgttcacga aggtcacgtt gccgctgaag ttatcgccgg taagaaacac   1020
tacttcgatc cgaaagttat cccgtccatc gcctataccg aaccagaagt tgcatgggta   1080
ggtctgactg agaaagaagc gaaagagaaa ggcatcagct atgaaaccgc caccttcccg   1140
tgggctgctt ctggtcgtgc tatcgcttcc gactgcgcag acggtatgac caagctgatt   1200
ttcgacaaag aatctcaccg tgtgatcggt ggtgcgattg tcggtaccaa cggcggcgag   1260
ctgctgggtg aaatcggcct ggcaatcgaa atgggttgtg atgctgaaga catcgcactg   1320
accatccacg cgcacccgac tctgcacgag tctgtgggcc tggcggcaga agtgttcgaa   1380
ggtagcatta ccgacctgcc gaacccgaaa gcgaagaaga agtaa                   1425
```

<210> SEQ ID NO 4
<211> LENGTH: 474
<212> TYPE: PRT
<213> ORGANISM: E.coli

<400> SEQUENCE: 4

```
Met Ser Thr Glu Ile Lys Thr Gln Val Val Leu Gly Ala Gly Pro
1               5                  10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Pro Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
```

```
                      225                 230                 235                 240
        Val Glu Ala Lys Glu Asp Gly Ile Tyr Val Thr Met Glu Gly Lys Lys
                          245                 250                 255

Ala Pro Ala Glu Pro Gln Arg Tyr Asp Ala Val Leu Val Ala Ile Gly
                260                 265                 270

Arg Val Pro Asn Gly Lys Asn Leu Asp Ala Gly Lys Ala Gly Val Glu
                    275                 280                 285

Val Asp Asp Arg Gly Phe Ile Arg Val Asp Lys Gln Leu Arg Thr Asn
                290                 295                 300

Val Pro His Ile Phe Ala Ile Gly Asp Ile Val Gly Gln Pro Met Leu
        305                 310                 315                 320

Ala His Lys Gly Val His Glu Gly His Val Ala Ala Glu Val Ile Ala
                        325                 330                 335

Gly Lys Lys His Tyr Phe Asp Pro Lys Val Ile Pro Ser Ile Ala Tyr
                        340                 345                 350

Thr Glu Pro Glu Val Ala Trp Val Gly Leu Thr Glu Lys Glu Ala Lys
                    355                 360                 365

Glu Lys Gly Ile Ser Tyr Glu Thr Ala Thr Phe Pro Trp Ala Ala Ser
                370                 375                 380

Gly Arg Ala Ile Ala Ser Asp Cys Ala Asp Gly Met Thr Lys Leu Ile
        385                 390                 395                 400

Phe Asp Lys Glu Ser His Arg Val Ile Gly Gly Ala Ile Val Gly Thr
                        405                 410                 415

Asn Gly Gly Glu Leu Leu Gly Glu Ile Gly Leu Ala Ile Glu Met Gly
                    420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
                    450                 455                 460

Asp Leu Pro Asn Pro Lys Ala Lys Lys Lys
        465                 470

<210> SEQ ID NO 5
<211> LENGTH: 2283
<212> TYPE: DNA
<213> ORGANISM: E.coli

<400> SEQUENCE: 5
atgtccgagc ttaatgaaaa gttagccaca gcctgggaag gttttaccaa aggtgactgg        60
cagaatgaag taaacgtccg tgacttcatt cagaaaaact acactccgta cgagggtgac       120
gagtccttcc tggctggcgc tactgaagcg accaccaccc tgtgggacaa agtaatggaa       180
ggcgttaaac tggaaaaccg cactcacgcg ccagttgact tgacaccgc tgttgcttcc        240 accatcacct ctcacgacgc tggctacatc aacaaagcgt ggaaaaagt tgttggtcta        300 cagactgaag ctccgctgaa acgtgctctt atcccgttcg gtggtatcaa aatgatcgag       360
ggttcctgca aagcgtacaa ccgcgaactg gacccgatga tcaaaaaaat cttcactgaa       420
taccgtaaaa ctcacaacca gggcgtgttc gacgtttaca ctccggacat cctgcgttgc       480
cgtaaatccg gtgttctgac cggtctgcca atgcttatg gccgtggccg tatcatcggt       540
gactaccgtc gcgttgcgct gtacggtatc gactacctga tgaaagacaa atacgctcag       600
ttcacctctc tgcaggctga tctgaaaaac ggctaaaacc tggaacagac tatccgtctg       660
cgcgaagaaa tcgctgaaca gcaccgcgct ctgggtcaga tgaaagaaat ggctgcgaaa       720
```

```
tacggctacg acatctctgg tccggctacc aacgctcagg aagctatcca gtggacttac      780
ttcggctacc tggctgctgt taagtctcag aacggtgctg caatgtcctt cggtcgtacc      840
tccaccttcc tggatgtgta catcgaacgt gacctgaaag ctggcaagat caccgaacaa      900
gaagcgcagg aaatggttga ccacctggtc atgaaactgc gtatggttcg cttcctgcgt      960
actccggaat acgatgaact gttctctggc gacccgatct gggcaaccga atctatcggt     1020
ggtatgggcc tcgacggtcg taccctggtt accaaaaaca gcttccgttt cctgaacacc     1080
ctgtacacca tgggtccgtc tccggaaccg aacatgacca ttctgtggtc tgaaaaactg     1140
ccgctgaact tcaagaaatt cgccgctaaa gtgtccatcg acacctcttc tctgcaatat     1200
gagaacgatg acctgatgcg tccggacttc aacaacgatg actacgctat gcttgctgc     1260
gtaagcccga tgatcgttgg taaacaaatg cagttcttcg gtgcgcgtgc aaacctggcg     1320
aaaaccatgc tgtacgcaat caacggcggc gttgacgaaa aactgaaaat gcaggttggt     1380
ccgaagtctg aaccgatcaa aggcgatgtc ctgaactatg atgaagtgat ggagcgcatg     1440
gatcacttca tggactggct ggctaaacag tacatcactg cactgaacat catccactac     1500
atgcacgaca gtacagcta cgaagcctct ctgatggcgc tgcacgaccg tgacgttatc     1560
cgcaccatgg cgtgtggtat cgctggtctg tccgttgctg ctgactccct gtctgcaatc     1620
aaatatgcga agttaaaacc gattcgtgac gaagacggtc tggctatcga cttcgaaatc     1680
gaaggcgaat acccgcagtt tggtaacaat gatccgcgtg tagatgacct ggctgttgac     1740
ctggtagaac gtttcatgaa gaaaattcag aaactgcaca cctaccgtga cgctatcccg     1800
actcagtctg ttctgaccat cacttctaac gttgtgtatg gtaagaaaac tggtaacacc     1860
ccagacggtc gtcgtgctgg cgcgccgttc ggaccgggtg ctaacccgat gcacggtcgt     1920
gaccagaaag tgctgtagc gtctctgact tccgttgcta aactaccgtt tgcttacgct     1980
aaagatggta tctcctacac cttctctatc gttccgaacg cactgggtaa agacgacgaa     2040
gttcgtaaga ccaacctggc tggtctgatg gatggttact ccaccacga agcatccatc     2100
gaaggtggtc agcacctgaa cgttaacgtg atgaaccgtg aaatgctgct cgacgcgatg     2160
gaaaacccgg aaaaatatcc gcagctgacc atccgtgtat ctggctacgc agtacgtttc     2220
aactcgctga ctaaagaaca gcagcaggac gttattactc gtaccttcac tcaatctatg     2280
taa                                                                   2283
```

<210> SEQ ID NO 6
<211> LENGTH: 760
<212> TYPE: PRT
<213> ORGANISM: E.coli

<400> SEQUENCE: 6

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Ala Leu Glu Lys
                85                  90                  95
```

-continued

Val Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
            115                 120                 125

Glu Leu Asp Pro Met Ile Lys Lys Ile Phe Thr Glu Tyr Arg Lys Thr
            130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Tyr Ala Gln Phe Thr Ser Leu Gln Ala Asp Leu
            195                 200                 205

Glu Asn Gly Val Asn Leu Glu Gln Thr Ile Arg Leu Arg Glu Glu Ile
            210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
            275                 280                 285

Glu Arg Asp Leu Lys Ala Gly Lys Ile Thr Glu Gln Glu Ala Gln Glu
            290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
            370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
            450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

```
Ala Leu His Asp Arg Asp Val Ile Arg Thr Met Ala Cys Gly Ile Ala
            515                 520                 525
Gly Leu Ser Val Ala Ala Asp Ser Leu Ser Ala Ile Lys Tyr Ala Lys
        530                 535                 540
Val Lys Pro Ile Arg Asp Glu Asp Gly Leu Ala Ile Asp Phe Glu Ile
545                 550                 555                 560
Glu Gly Glu Tyr Pro Gln Phe Gly Asn Asn Asp Pro Arg Val Asp Asp
                565                 570                 575
Leu Ala Val Asp Leu Val Glu Arg Phe Met Lys Lys Ile Gln Lys Leu
            580                 585                 590
His Thr Tyr Arg Asp Ala Ile Pro Thr Gln Ser Val Leu Thr Ile Thr
        595                 600                 605
Ser Asn Val Val Tyr Gly Lys Lys Thr Gly Asn Thr Pro Asp Gly Arg
    610                 615                 620
Arg Ala Gly Ala Pro Phe Gly Pro Gly Ala Asn Pro Met His Gly Arg
625                 630                 635                 640
Asp Gln Lys Gly Ala Val Ala Ser Leu Thr Ser Val Ala Lys Leu Pro
                645                 650                 655
Phe Ala Tyr Ala Lys Asp Gly Ile Ser Tyr Thr Phe Ser Ile Val Pro
            660                 665                 670
Asn Ala Leu Gly Lys Asp Asp Glu Val Arg Lys Thr Asn Leu Ala Gly
        675                 680                 685
Leu Met Asp Gly Tyr Phe His His Glu Ala Ser Ile Glu Gly Gly Gln
    690                 695                 700
His Leu Asn Val Asn Val Met Asn Arg Glu Met Leu Leu Asp Ala Met
705                 710                 715                 720
Glu Asn Pro Glu Lys Tyr Pro Gln Leu Thr Ile Arg Val Ser Gly Tyr
                725                 730                 735
Ala Val Arg Phe Asn Ser Leu Thr Lys Glu Gln Gln Gln Asp Val Ile
            740                 745                 750
Thr Arg Thr Phe Thr Gln Ser Met
        755                 760

<210> SEQ ID NO 7
<211> LENGTH: 2676
<212> TYPE: DNA
<213> ORGANISM: E.coli

<400> SEQUENCE: 7
atggctgtta ctaatgtcgc tgaacttaac gcactcgtag agcgtgtaaa aaaagcccag      60
cgtgaatatg ccagtttcac tcaagagcaa gtagacaaaa tcttccgcgc cgccgctctg     120
gctgctgcag atgctcgaat cccactcgcg aaaatggccg ttgccgaatc cggcatgggt     180
atcgtcgaag ataaagtgat caaaaaccac tttgcttctg aatatatcta caacgcctat     240
aaagatgaaa aacctgtggt gttctgtctc gaagacgaca cttttggtac catcactatc     300
gctgaaccaa tcggtattat tgcggtatcg gttccgacca ctaacccgac ttcaactgct     360
atcttcaaat cgctgatcag tctgaagacc cgtaacgcca ttatcttctc cccgcacccg     420
cgtgcaaaag atgccaccaa aaagcggct gatatcgttc tgcaggctgc tatcgctgcc     480
ggtgctccga agatctgat cggctggatc gatcaacctt ctgttgaact gtctaacgca     540
ctgatgcacc acccagacat caacctgatc ctcgcgactg gtggtccggg catggttaaa     600
gccgcataca gctccggtaa accagctatc ggtgtaggcg cgggcaacac tccagttgtt     660
atcgatgaaa ctgctgatat caaacgtgca gttgcatctg tactgatgtc caaaaccttc     720
```

```
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggctcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg ttatgctga tcagatcact    1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg tggtggttc cccgatggac gccgcgaaga tcatgtgggt tatgtacgaa   1680
catccggaaa ctcacttcga gagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggg ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcgtt cgatgaccag   2520
tgcaccggcg ctaacccgcg ttacccgctg atctccgagc tgaaacagat cctgctggat   2580
acctactacg gtcgtgatta tgtagaaggt gaaactgcag cgaaaaaaga gccgctccg   2640
gctaaagctg agaaaaaagc gaaaaaatcc gcttaa                              2676
```

<210> SEQ ID NO 8
<211> LENGTH: 891
<212> TYPE: PRT
<213> ORGANISM: E.coli

<400> SEQUENCE: 8

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp

```
            20              25              30
Lys Ile Phe Arg Ala Ala Ala Leu Ala Ala Ala Asp Ala Arg Ile Pro
            35              40              45
Leu Ala Lys Met Ala Val Ala Glu Ser Gly Met Gly Ile Val Glu Asp
            50              55              60
Lys Val Ile Lys Asn His Phe Ala Ser Glu Tyr Ile Tyr Asn Ala Tyr
 65              70              75              80
Lys Asp Glu Lys Thr Cys Gly Val Leu Ser Glu Asp Thr Phe Gly
                85              90              95
Thr Ile Thr Ile Ala Glu Pro Ile Gly Ile Cys Gly Ile Val Pro
            100             105             110
Thr Thr Asn Pro Thr Ser Thr Ala Ile Phe Lys Ser Leu Ile Ser Leu
            115             120             125
Lys Thr Arg Asn Ala Ile Ile Phe Ser Pro His Pro Arg Ala Lys Asp
            130             135             140
Ala Thr Asn Lys Ala Ala Asp Ile Val Leu Gln Ala Ala Ile Ala Ala
145             150             155             160
Gly Ala Pro Lys Asp Leu Ile Gly Trp Ile Asp Gln Pro Ser Val Glu
                165             170             175
Leu Ser Asn Ala Leu Met His His Pro Asp Ile Asn Leu Ile Leu Ala
            180             185             190
Thr Gly Gly Pro Gly Met Val Lys Ala Ala Tyr Ser Ser Gly Lys Pro
            195             200             205
Ala Ile Gly Val Gly Ala Gly Asn Thr Pro Val Val Ile Asp Glu Thr
            210             215             220
Ala Asp Ile Lys Arg Ala Val Ala Ser Val Leu Met Ser Lys Thr Phe
225             230             235             240
Asp Asn Gly Val Ile Cys Ala Ser Glu Gln Ser Val Val Val Asp
                245             250             255
Ser Val Tyr Asp Ala Val Arg Glu Arg Phe Ala Thr His Gly Gly Tyr
            260             265             270
Leu Leu Gln Gly Lys Glu Leu Lys Ala Val Gln Asp Val Ile Leu Lys
            275             280             285
Asn Gly Ala Leu Asn Ala Ala Ile Val Gly Gln Pro Ala Tyr Lys Ile
            290             295             300
Ala Glu Leu Ala Gly Phe Ser Val Pro Glu Asn Thr Lys Ile Leu Ile
305             310             315             320
Gly Glu Val Thr Val Val Asp Glu Ser Glu Pro Phe Ala His Glu Lys
                325             330             335
Leu Ser Pro Thr Leu Ala Met Tyr Arg Ala Lys Asp Phe Glu Asp Ala
            340             345             350
Val Glu Lys Ala Glu Lys Leu Val Ala Met Gly Gly Ile Gly His Thr
            355             360             365
Ser Cys Leu Tyr Thr Asp Gln Asp Asn Gln Pro Ala Arg Val Ser Tyr
            370             375             380
Phe Gly Gln Lys Met Lys Thr Ala Arg Ile Leu Ile Asn Thr Pro Ala
385             390             395             400
Ser Gln Gly Gly Ile Gly Asp Leu Tyr Asn Phe Lys Leu Ala Pro Ser
                405             410             415
Leu Thr Leu Gly Cys Gly Ser Trp Gly Gly Asn Ser Ile Ser Glu Asn
            420             425             430
Val Gly Pro Lys His Leu Ile Asn Lys Lys Thr Val Ala Lys Arg Ala
            435             440             445
```

```
Glu Asn Met Leu Trp His Lys Leu Pro Lys Ser Ile Tyr Phe Arg Arg
    450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
        515                 520                 525
Ala Glu Leu Ala Asn Ser Phe Lys Pro Asp Val Ile Ala Leu Gly
    530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
                565                 570                 575
Arg Lys Arg Ile Tyr Lys Phe Pro Lys Met Gly Val Lys Ala Lys Met
            580                 585                 590
Ile Ala Val Thr Thr Thr Ser Gly Thr Gly Ser Glu Val Thr Pro Phe
        595                 600                 605
Ala Val Val Thr Asp Asp Ala Thr Gly Gln Lys Tyr Pro Leu Ala Asp
    610                 615                 620
Tyr Ala Leu Thr Pro Asp Met Ala Ile Val Asp Ala Asn Leu Val Met
625                 630                 635                 640
Asp Met Pro Lys Ser Leu Cys Ala Phe Gly Gly Leu Asp Ala Val Thr
                645                 650                 655
His Ala Met Glu Ala Tyr Val Ser Val Leu Ala Ser Glu Phe Ser Asp
            660                 665                 670
Gly Gln Ala Leu Gln Ala Leu Lys Leu Leu Lys Glu Tyr Leu Pro Ala
        675                 680                 685
Ser Tyr His Glu Gly Ser Lys Asn Pro Val Ala Arg Glu Arg Val His
    690                 695                 700
Ser Ala Ala Thr Ile Ala Gly Ile Ala Phe Ala Asn Ala Phe Leu Gly
705                 710                 715                 720
Val Cys His Ser Met Ala His Lys Leu Gly Ser Gln Phe His Ile Pro
                725                 730                 735
His Gly Leu Ala Asn Ala Leu Leu Ile Cys Asn Val Ile Arg Tyr Asn
            740                 745                 750
Ala Asn Asp Asn Pro Thr Lys Gln Thr Ala Phe Ser Gln Tyr Asp Arg
        755                 760                 765
Pro Gln Ala Arg Arg Arg Tyr Ala Glu Ile Ala Asp His Leu Gly Leu
    770                 775                 780
Ser Ala Pro Gly Asp Arg Thr Ala Ala Lys Ile Glu Lys Leu Leu Ala
785                 790                 795                 800
Trp Leu Glu Thr Leu Lys Ala Glu Leu Gly Ile Pro Lys Ser Ile Arg
                805                 810                 815
Glu Ala Gly Val Gln Glu Ala Asp Phe Leu Ala Asn Val Asp Lys Leu
            820                 825                 830
Ser Glu Asp Ala Phe Asp Asp Gln Cys Thr Gly Ala Asn Pro Arg Tyr
        835                 840                 845
Pro Leu Ile Ser Glu Leu Lys Gln Ile Leu Leu Asp Thr Tyr Tyr Gly
    850                 855                 860
```

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 9
<211> LENGTH: 990
<212> TYPE: DNA
<213> ORGANISM: E.coli

<400> SEQUENCE: 9

| | | | | | | |
|---|---|---|---|---|---|---|
| atgaaactcg | ccgtttatag | cacaaaacag | tacgacaaga | agtacctgca | acaggtgaac | 60 |
| gagtccttttg | gctttgagct | ggaattttttt | gactttctgc | tgacggaaaa | aaccgctaaa | 120 |
| actgccaatg | gctgcgaagc | ggtatgtatt | ttcgtaaacg | atgacggcag | ccgcccggtg | 180 |
| ctggaagagc | tgaaaaagca | cggcgttaaa | tatatcgccc | tgcgctgtgc | cggtttcaat | 240 |
| aacgtcgacc | ttgacgcggc | aaaagaactg | gggctgaaag | tagtccgtgt | tccagcctat | 300 |
| gatccagagg | ccgttgctga | acacgccatc | ggtatgatga | tgacgctgaa | ccgccgtatt | 360 |
| caccgcgcgt | atcagcgtac | ccgtgacgct | aacttctctc | tggaaggtct | gaccggcttt | 420 |
| actatgtatg | caaaacggc | aggcgttatc | ggtaccggta | aaatcggtgt | ggcgatgctg | 480 |
| cgcattctga | aggttttgg | tatgcgtctg | ctggcgttcg | atccgtatcc | aagtgcagcg | 540 |
| gcgctggaac | tcggtgtgga | gtatgtcgat | ctgccaaccc | tgttctctga | atcagacgtt | 600 |
| atctctctgc | actgcccgct | gacaccggaa | aactaccatc | tgttgaacga | agccgccttc | 660 |
| gatcagatga | aaaatggcgt | gatgatcgtc | aataccagtc | gcggtgcatt | gattgattct | 720 |
| caggcagcaa | ttgaagcgct | gaaaaatcag | aaaattggtt | cgttgggtat | ggacgtgtat | 780 |
| gagaacgaac | gcgatctatt | ctttgaagat | aaatccaacg | acgtaattca | ggatgacgta | 840 |
| ttccgtcgcc | tgtctgcctg | ccacaacgtg | ctatttaccg | gcaccaggc | attcctgaca | 900 |
| gcagaagctc | tgaccagtat | ttctcagact | acgctgcaaa | acttaagcaa | tctggaaaaa | 960 |
| ggcgaaacct | gcccgaacga | actggtttaa | | | | 990 |

<210> SEQ ID NO 10
<211> LENGTH: 329
<212> TYPE: PRT
<213> ORGANISM: E.coli

<400> SEQUENCE: 10

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
                20                  25                  30

Leu Leu Thr Glu Lys Thr Ala Lys Thr Ala Asn Gly Cys Glu Ala Val
            35                  40                  45

Cys Ile Phe Val Asn Asp Asp Gly Ser Arg Pro Val Leu Glu Glu Leu
        50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
                100                 105                 110

Met Met Thr Leu Asn Arg Arg Ile His Arg Ala Tyr Gln Arg Thr Arg
            115                 120                 125

```
Asp Ala Asn Phe Ser Leu Glu Gly Leu Thr Gly Phe Thr Met Tyr Gly
        130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
                180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Asp Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
                260                 265                 270

Asn Asp Val Ile Gln Asp Asp Val Phe Arg Arg Leu Ser Ala Cys His
            275                 280                 285

Asn Val Leu Phe Thr Gly His Gln Ala Phe Leu Thr Ala Glu Ala Leu
        290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 11
<211> LENGTH: 2145
<212> TYPE: DNA
<213> ORGANISM: E.coli

<400> SEQUENCE: 11
gtgtcccgta ttattatgct gatccctacc ggaaccagcg tcggtctgac cagcgtcagc        60
cttggcgtga tccgtgcaat ggaacgcaaa ggcgttcgtc tgagcgtttt caaacctatc       120
gctcagccgc gtaccggtgg cgatgcgccc gatcagacta cgactatcgt gcgtgcgaac       180
tcttccacca cgacggccgc tgaaccgctg aaaatgagct acgttgaagg tctgctttcc       240
agcaatcaga agatgtgct gatggaagag atcgtcgcaa actaccacgc taacaccaaa       300
gacgctgaag tcgttctggt tgaaggtctg gtcccgacac gtaagcacca gtttgcccag       360
tctctgaact acgaaatcgc taaaacgctg aatgcggaaa tcgtcttcgt tatgtctcag       420
ggcactgaca ccccggaaca gctgaaagag cgtatcgaac tgacccgcaa cagcttcggc       480
ggtgccaaaa acaccaacat caccggcgtt atcgttaaca aactgaacgc accggttgat       540
gaacagggtc gtactcgccc ggatctgtcc gagattttcg acgactcttc caaagctaaa       600
gtaaacaatg ttgatccggc gaagctgcaa gaatccagcc cgctgccggt tctcggcgct       660
gtgccgtgga ctttgacct gatcgcgact cgtgcgatcg atatggctcg ccacctgaat       720
gcgaccatca tcaacgaagg cgacatcaat actcgccgcg ttaaatccgt cactttctgc       780
gcacgcagca ttccgcacat gctggagcac ttccgtgccg ttctctgct ggtgacttcc       840 gcagaccgtc ctgacgtgct ggtggccgct tgcctggcag ccatgaacgg cgtagaaatc       900
ggtgccctgc tgctgactgg cggctacgaa atggacgcgc gcatttctaa actgtgcgaa       960
```

-continued

```
cgtgctttcg ctaccggcct gccggtattt atggtgaaca ccaacacctg gcagacctct   1020
ctgagcctgc agagcttcaa cctggaagtt ccggttgacg atcacgagcg tatcgagaaa   1080
gttcaggaat acgttgctaa ctacatcaac gctgactgga tcgaatctct gactgccact   1140
tctgagcgca gccgtcgtct gtctccgcct gcgttccgtt atcagctgac tgaacttgcg   1200
cgcaaagcgg gcaaacgtat cgtactgccg gaaggtgacg aaccgcgtac cgttaaagca   1260
gccgctatct gtgctgaacg tggtatcgca acttgcgtac tgctgggtaa tccggcagag   1320
atcaaccgtg ttgcagcgtc tcagggtgta gaactgggtg cagggattga aatcgttgat   1380
ccagaagtgg ttcgcgaaag ctatgttggt cgtctggtcg aactgcgtaa gaacaaaggc   1440
atgaccgaaa ccgttgcccg cgaacagctg gaagacaacg tggtgctcgg tacgctgatg   1500
ctggaacagg atgaagttga tggtctggtt ccggtgctg ttcacactac cgcaaacacc   1560
atccgtccgc cgctgcagct gatcaaaact gcaccgggca gctccctggt atcttccgtg   1620
ttcttcatgc tgctgccgga acaggtttac gtttacggtg actgtgcgat caacccggat   1680
ccgaccgctg aacagctggc agaaatcgcg attcagtccg ctgattccgc tgcggccttc   1740
ggtatcgaac gcgcgttgc tatgctctcc tactccaccg gtacttctgg tgcaggtagc   1800
gacgtagaaa aagttcgcga agcaactcgt ctggcgcagg aaaaacgtcc tgacctgatg   1860
atcgacggtc cgctgcagta cgacgctgcg gtaatggctg acgttgcgaa atccaaagcg   1920
ccgaactctc cggttgcagg tcgcgctacc gtgttcatct cccggatct gaacaccggt   1980
aacaccacct acaaagcggt acagcgttct gccgacctga tctccatcgg gccgatgctg   2040
cagggtatgc gcaagccggt taacgacctg tcccgtggcg cactggttga cgatatcgtc   2100
tacaccatcg cgctgactgc gattcagtct gcacagcagc agtaa             2145
```

<210> SEQ ID NO 12
<211> LENGTH: 714
<212> TYPE: PRT
<213> ORGANISM: E.coli

<400> SEQUENCE: 12

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160
```

-continued

Gly Ala Lys Asn Thr Asn Ile Thr Gly Val Ile Asn Lys Leu Asn
            165                 170                 175

Ala Pro Val Asp Glu Gln Gly Arg Thr Arg Pro Asp Leu Ser Glu Ile
        180                 185                 190

Phe Asp Asp Ser Ser Lys Ala Lys Val Asn Asn Val Asp Pro Ala Lys
            195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
    370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
    450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
    530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser

```
              580                 585                 590
Thr Gly Thr Ser Gly Ala Gly Ser Asp Val Glu Lys Val Arg Glu Ala
                595                 600                 605

Thr Arg Leu Ala Gln Glu Lys Arg Pro Asp Leu Met Ile Asp Gly Pro
            610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
                660                 665                 670

Leu Ile Ser Ile Gly Pro Met Leu Gln Gly Met Arg Lys Pro Val Asn
                675                 680                 685

Asp Leu Ser Arg Gly Ala Leu Val Asp Asp Ile Val Tyr Thr Ile Ala
                690                 695                 700

Leu Thr Ala Ile Gln Ser Ala Gln Gln Gln
705                 710

<210> SEQ ID NO 13
<211> LENGTH: 1809
<212> TYPE: DNA
<213> ORGANISM: E.coli

<400> SEQUENCE: 13
gtgcaaacct tcaagccga tcttgccatt gtaggcgccg gtggcgcggg attacgtgct       60
gcaattgctg ccgcgcaggc aaatccgaat gcaaaaatcg cactaatctc aaaagtatac     120
ccgatgcgta gccataccgt tgctgcagaa gggggctccg ccgctgtcgc gcaggatcat     180
gacagcttcg aatatcactt tcacgataca gtagcgggtg cgactggtt gtgtgagcag      240
gatgtcgtgg attatttcgt ccaccactgc ccaaccgaaa tgacccaact ggaactgtgg     300
ggatgcccat ggagccgtcg cccggatggt agcgtcaacg tacgtcgctt cggcggcatg     360
aaaatcgagc gcacctggtt cgccgccgat aagaccggct tccatatgct gcacacgctg     420
ttccagacct ctctgcaatt cccgcagatc cagcgttttg acgaacattt cgtgctggat     480
attctggttg atgatggtca tgttcgcggc ctggtagcaa tgaacatgat ggaaggcacg     540
ctggtgcaga tccgtgctaa cgcggtcgtt atggctactg gcggtgcggg tcgcgtttat     600
cgttacaaca ccaacggcgg catcgttacc ggtgacggta tgggtatggc gctaagccac     660
ggcgttccgc tgcgtgacat ggaattcgtt cagtatcacc caaccggtct gccaggttcc     720
ggtatcctga tgaccgaagg ctgccgcggt gaaggcggta ttctggtcaa caaaaatggc     780
taccgttatc tgcaagatta cggcatgggc cggaaactc gctgggcga ccgaaaaac      840
aaatatatgg aactgggtcc acgcgacaaa gtttctcagg ccttctggca cgaatggcgt     900
aaaggcaaca ccatctccac gccgcgtggc gatgtggttt atctcgacct gcgtcacctc    960
ggcgagaaaa aactgcatga acgtctgccg ttcatctgcg aactggcgaa agcgtacgtt    1020
ggcgtcgatc cggttaaaga accgattccg gtacgtccga ccgcacacta ccatgggc     1080
ggtatcgaaa ccgatcagaa ctgtgaaacc cgcattaaag tctgttcgc cgtgggtgaa    1140
tgttcctctg ttggtctgca cggtgcaaac cgtctgggtt ctaactccct ggcggaactg    1200
gtggtcttcg ccgtctggcc ggtgaacaa gcgacagagc gtgcagcaac tgccggtaat    1260
ggcaacgaag cggcaattga agcgcaggca gctggcgttg aacaacgtct gaagatctg     1320
gttaaccagg atggcggcga aaactgggcg aagatccgcg acgaaatggg cctggcaatg    1380
```

-continued

```
gaagaaggtt gcggtatcta ccgtacgccg gaactgatgc agaaaaccat cgacaagctg      1440
gcagagctgc aggaacgctt caagcgcgtg cgcatcaccg acacctccag cgtgttcaac      1500
accgacctgc tctacaccat tgaactgggc cacggtctga cgttgctga atgtatggcg       1560 cactccgcaa tggcacgtaa agagtcccgc ggcgcacacc agcgtctgga cgaaggttgc      1620
accgagcgtg acgacgtcaa cttcctcaaa cacaccctcg ccttccgcga tgctgatggc      1680
acgactcgcc tggagtacag cgacgtgaag attactacgc tgccgccagc taaacgcgtt      1740
tacggtggcg aagcggatgc agccgataag gcggaagcag ccaataagaa ggagaaggcg      1800
aatggctga                                                              1809
```

<210> SEQ ID NO 14
<211> LENGTH: 602
<212> TYPE: PRT
<213> ORGANISM: E.coli

<400> SEQUENCE: 14

```
Met Gln Thr Phe Gln Ala Asp Leu Ala Ile Val Gly Ala Gly Gly Ala
1               5                   10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
        275                 280                 285
```

```
Asp Lys Val Ser Gln Ala Phe Trp His Glu Trp Arg Lys Gly Asn Thr
    290                 295                 300
Ile Ser Thr Pro Arg Gly Asp Val Val Tyr Leu Asp Leu Arg His Leu
305                 310                 315                 320
Gly Glu Lys Lys Leu His Glu Arg Leu Pro Phe Ile Cys Glu Leu Ala
                325                 330                 335
Lys Ala Tyr Val Gly Val Asp Pro Val Lys Glu Pro Ile Pro Val Arg
                340                 345                 350
Pro Thr Ala His Tyr Thr Met Gly Gly Ile Glu Thr Asp Gln Asn Cys
                355                 360                 365
Glu Thr Arg Ile Lys Gly Leu Phe Ala Val Gly Glu Cys Ser Ser Val
370                 375                 380
Gly Leu His Gly Ala Asn Arg Leu Gly Ser Asn Ser Leu Ala Glu Leu
385                 390                 395                 400
Val Val Phe Gly Arg Leu Ala Gly Glu Gln Ala Thr Glu Arg Ala Ala
                405                 410                 415
Thr Ala Gly Asn Gly Asn Glu Ala Ala Ile Glu Ala Gln Ala Ala Gly
                420                 425                 430
Val Glu Gln Arg Leu Lys Asp Leu Val Asn Gln Asp Gly Gly Glu Asn
                435                 440                 445
Trp Ala Lys Ile Arg Asp Glu Met Gly Leu Ala Met Glu Glu Gly Cys
450                 455                 460
Gly Ile Tyr Arg Thr Pro Glu Leu Met Gln Lys Thr Ile Asp Lys Leu
465                 470                 475                 480
Ala Glu Leu Gln Glu Arg Phe Lys Arg Val Arg Ile Thr Asp Thr Ser
                485                 490                 495
Ser Val Phe Asn Thr Asp Leu Leu Tyr Thr Ile Glu Leu Gly His Gly
                500                 505                 510
Leu Asn Val Ala Glu Cys Met Ala His Ser Ala Met Ala Arg Lys Glu
            515                 520                 525
Ser Arg Gly Ala His Gln Arg Leu Asp Glu Gly Cys Thr Glu Arg Asp
530                 535                 540
Asp Val Asn Phe Leu Lys His Thr Leu Ala Phe Arg Asp Ala Asp Gly
545                 550                 555                 560
Thr Thr Arg Leu Glu Tyr Ser Asp Val Lys Ile Thr Thr Leu Pro Pro
                565                 570                 575
Ala Lys Arg Val Tyr Gly Gly Glu Ala Asp Ala Ala Asp Lys Ala Glu
                580                 585                 590
Ala Ala Asn Lys Lys Glu Lys Ala Asn Gly
            595                 600

<210> SEQ ID NO 15
<211> LENGTH: 1119
<212> TYPE: DNA
<213> ORGANISM: G.stearothermophilus

<400> SEQUENCE: 15
atgaaaattg gcatccctaa agagattaag aacaatgaaa accgtgtagc aatcaccccg      60
gcaggtgtta tgactctggt taaagcgggc cacgatgtgt acgtcgaaac cgaagcgggt     120
gccggcagcg gcttcagcga cagcgagtat gagaaggcgg gtgcggttat tgtgactaag     180
gcggaggacg cttgggcagc cgaaatggtt ctgaaggtga agaaccgct ggcggaggag      240 tttcgctatt ttcgtccggg tctgattttg ttcacctacc tgcacctggc tgcggccgag     300
gcgctgacca aggcactggt ggagcagaag gttgttggca tcgcgtacga aacggttcaa     360
```

```
ctggcgaatg gttccctgcc gctgctgacc cctatgtctg aagttgcggg tcgcatgagc    420
gttcaagtcg gcgctcagtt tctggagaaa ccgcacggtg caagggcat tttgctgggt    480 ggtgttccgg gtgtccgccg tggtaaagtg acgatcattg cggtggtac ggccggtacg    540 aacgcggcca agattgccgt aggtctgggt gcagatgtga ccattctgga catcaacgcg    600
gaacgtttgc gtgagctgga cgacctgttt ggcgaccaag tcaccaccct gatgagcaac    660
agctaccaca tcgcggagtg cgtccgtgaa agcgatttgg tcgttggtgc ggtgctgatc    720
ccgggtgcaa agccccgaa actggtgacc gaggagatgg tccgtagcat gaccccgggt    780
tcggttctgg tcgacgtggc aattgaccag ggcggtatct tcgaaaccac cgaccgcgtc    840
acgacccatg atgacccgac ctatgtgaaa catggcgtgg ttcactatgc ggtcgcgaat    900
atgccgggtg cagtgccgcg cacgtccacg ttcgcgctga cgaacgtgac gattccatac    960
gctctgcaga tcgccaataa gggctatcgt gcggcgtgtc tggataatcc ggcattgctg   1020
aaaggcatca ataccctgga tggtcatatc gtttacgagg ctgtggctgc agcacacaac   1080
atgccgtaca ctgatgtcca tagcttgctg caaggctaa                          1119
```

<210> SEQ ID NO 16
<211> LENGTH: 372
<212> TYPE: PRT
<213> ORGANISM: G.stearothermophilus

<400> SEQUENCE: 16

```
Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
                20                  25                  30

Val Tyr Val Glu Thr Glu Ala Gly Ala Gly Ser Gly Phe Ser Asp Ser
            35                  40                  45

Glu Tyr Glu Lys Ala Gly Ala Val Ile Val Thr Lys Ala Glu Asp Ala
        50                  55                  60

Trp Ala Ala Glu Met Val Leu Lys Val Lys Glu Pro Leu Ala Glu Glu
65                  70                  75                  80

Phe Arg Tyr Phe Arg Pro Gly Leu Ile Leu Phe Thr Tyr Leu His Leu
                85                  90                  95

Ala Ala Ala Glu Ala Leu Thr Lys Ala Leu Val Glu Gln Lys Val Val
            100                 105                 110

Gly Ile Ala Tyr Glu Thr Val Gln Leu Ala Asn Gly Ser Leu Pro Leu
        115                 120                 125

Leu Thr Pro Met Ser Glu Val Ala Gly Arg Met Ser Val Gln Val Gly
    130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Ala Lys Ile Ala Val Gly Leu Gly Ala Asp
            180                 185                 190

Val Thr Ile Leu Asp Ile Asn Ala Glu Arg Leu Arg Glu Leu Asp Asp
        195                 200                 205

Leu Phe Gly Asp Gln Val Thr Thr Leu Met Ser Asn Ser Tyr His Ile
    210                 215                 220

Ala Glu Cys Val Arg Glu Ser Asp Leu Val Val Gly Ala Val Leu Ile
225                 230                 235                 240
```

```
Pro Gly Ala Lys Ala Pro Lys Leu Val Thr Glu Met Val Arg Ser
            245                 250                 255
Met Thr Pro Gly Ser Val Leu Val Asp Val Ala Ile Asp Gln Gly Gly
        260                 265                 270
Ile Phe Glu Thr Thr Asp Arg Val Thr Thr His Asp Asp Pro Thr Tyr
        275                 280                 285
Val Lys His Gly Val Val His Tyr Ala Val Ala Asn Met Pro Gly Ala
        290                 295                 300
Val Pro Arg Thr Ser Thr Phe Ala Leu Thr Asn Val Thr Ile Pro Tyr
305                 310                 315                 320
Ala Leu Gln Ile Ala Asn Lys Gly Tyr Arg Ala Ala Cys Leu Asp Asn
            325                 330                 335
Pro Ala Leu Leu Lys Gly Ile Asn Thr Leu Asp Gly His Ile Val Tyr
        340                 345                 350
Glu Ala Val Ala Ala Ala His Asn Met Pro Tyr Thr Asp Val His Ser
        355                 360                 365
Leu Leu Gln Gly
    370

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
actgcggtag ttcttcactg                                          20

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
agtacctttc tggtttagcc g                                        21

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
gatagcagaa acggaaccac                                          20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
ggtgctgttc acactaccgc                                          20

<210> SEQ ID NO 21
<211> LENGTH: 20
```

```
<212> TYPE: DNA
<213> ORGANISM: Artificial
<220> FEATURE:
<223> OTHER INFORMATION: Primer

<400> SEQUENCE: 21
tgacgagatt actgctgctg                                              20

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
atttccggtt cagatatccg c                                            21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
gggttgacca gcgcaaataa c                                            21

<210> SEQ ID NO 24
<211> LENGTH: 23
<212> TYPE: DNA
<213> ORGANISM: Artificial
<220> FEATURE:
<223> OTHER INFORMATION: Primer

<400> SEQUENCE: 24
cagaagtgag taatcttgct tac                                          23

<210> SEQ ID NO 25
<211> LENGTH: 23
<212> TYPE: DNA
<213> ORGANISM: Artificial
<220> FEATURE:
<223> OTHER INFORMATION: Primer

<400> SEQUENCE: 25
gatcacttta tcttcgacga tac                                          23

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
gcgaacgtgg ataaactgtc tg                                           22

<210> SEQ ID NO 27
<211> LENGTH: 22
<212> TYPE: DNA
<213> ORGANISM: Artificial
<220> FEATURE:
<223> OTHER INFORMATION: Primer

<400> SEQUENCE: 27
```

```
gctcttaagc accgacgttg ac                                            22

<210> SEQ ID NO 28
<211> LENGTH: 22
<212> TYPE: DNA
<213> ORGANISM: Artificial
<220> FEATURE:
<223> OTHER INFORMATION: Primer

<400> SEQUENCE: 28
gtcggctcat taacggctat tc                                            22

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gacggatctc cgccataatc                                               20

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
tcgccacccg ctactgtatc                                               20

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
caaagcgttc tgacgaaccg g                                             21

<210> SEQ ID NO 32
<211> LENGTH: 22
<212> TYPE: DNA
<213> ORGANISM: Artificial
<220> FEATURE:
<223> OTHER INFORMATION: Primer

<400> SEQUENCE: 32
tgtgcgatgc acaatatcgt tg                                            22

<210> SEQ ID NO 33
<211> LENGTH: 21
<212> TYPE: DNA
<213> ORGANISM: Artificial
<220> FEATURE:
<223> OTHER INFORMATION: Primer

<400> SEQUENCE: 33
ttggttgggt tgacatactg g                                             21

<210> SEQ ID NO 34
<211> LENGTH: 21
<212> TYPE: DNA
<213> ORGANISM: Artificial
```

```
<220> FEATURE:
<223> OTHER INFORMATION: Primer

<400> SEQUENCE: 34
tgaacttcat cactgataac c                                              21

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
ttcaaaggag tgaatgcgac c                                              21

<210> SEQ ID NO 36
<211> LENGTH: 22
<212> TYPE: DNA
<213> ORGANISM: Artificial
<220> FEATURE:
<223> OTHER INFORMATION: Primer

<400> SEQUENCE: 36
gtcgcggtta tgacaataca gg                                             22

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
taccgtgccg acgttcaata ac                                             22

<210> SEQ ID NO 38
<211> LENGTH: 21
<212> TYPE: DNA
<213> ORGANISM: Artificial
<220> FEATURE:
<223> OTHER INFORMATION: Primer

<400> SEQUENCE: 38
catcagcagg cttagcgcaa c                                              21

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
acctttacgc gtaatgcgtg                                                20

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
accgtttacg ctttccagca c                                              21
```

<210> SEQ ID NO 41
<211> LENGTH: 22
<212> TYPE: DNA
<213> ORGANISM: Artificial
<220> FEATURE:
<223> OTHER INFORMATION: Primer

<400> SEQUENCE: 41
cgaattatcg atctcgctca ac    22

<210> SEQ ID NO 42
<211> LENGTH: 23
<212> TYPE: DNA
<213> ORGANISM: Artificial
<220> FEATURE:
<223> OTHER INFORMATION: Primer

<400> SEQUENCE: 42
cgtctatatt gctgaaggta cag    23

<210> SEQ ID NO 43
<211> LENGTH: 21
<212> TYPE: DNA
<213> ORGANISM: Artificial
<220> FEATURE:
<223> OTHER INFORMATION: Primer

<400> SEQUENCE: 43
tcgaaggtcc attcacgcaa c    21

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
gattcccacc gcaacgttag    20

<210> SEQ ID NO 45
<211> LENGTH: 1095
<212> TYPE: DNA
<213> ORGANISM: Escherichia coli

<400> SEQUENCE: 45
atggcacaac agactccttt gtacgaacaa cacacgcttt gcggcgctcg catggtggat    60
ttccacggct ggatgatgcc gctgcattac ggttcgcaaa tcgacgaaca tcatgcggta    120
cgtaccgatg ccggaatgtt tgatgtgtca catatgacca tcgtcgatct ccgcggcagc    180
cgcacccggg agtttctgcg ttatctgctg gcgaacgatg tggcgaagct caccaaaagc    240
ggcaaagccc tttactcggg gatgttgaat gcctctggcg gtgtgataga tgacctcatc    300
gtctactact ttactgaaga tttcttccgc ctcgttgtta actccgccac ccgcgaaaaa    360
gacctctcct ggattaccca acacgctgaa cctttcggca tcgaaattac cgttcgtgat    420
gacctttcca tgattgccgt gcaagggccg aatgcgcagg caaaagctgc cacactgttt    480
aatgacgccc agcgtcaggc ggtggaaggg atgaaaccgt tctttggcgt gcaggcgggc    540
gatctgttta ttgccaccac tggttatacc ggtgaagcgg gctatgaaat tgcgctgccc    600
aatgaaaaag cggccgattt ctggcgtgcg ctggtggaag cgggtgttaa gccatgtggc    660
ttgggcgcgc gtgacacgct gcgtctggaa gcgggcatga atctttatgg tcaggagatg    720

```
gacgaaacta tttctccttt agccgccaac atgggctgga ctatcgcctg ggaaccggca    780
gatcgtgact ttatcggtcg tgaagccctg aagtgcagc gtgagcatgg tacagaaaaa     840
ctggttggtc tggtgatgac cgaaaaaggc gtgctgcgta atgaactgcc ggtacgcttt    900
accgatgcgc aggcaaccag atgaaggc attatcacca gcggtacttt ctccccgacg      960
ctgggttaca gcattgcgct ggcgcgcgtg ccggaaggta ttggcgaaac ggcgattgtg   1020
caaattcgca accgtgaaat gccggttaaa gtgacaaaac tgttttttgt gcgtaacggc   1080
aaagccgtcg cgtga                                                    1095
```

<210> SEQ ID NO 46
<211> LENGTH: 364
<212> TYPE: PRT
<213> ORGANISM: Escherichia coli

<400> SEQUENCE: 46

```
Met Ala Gln Gln Thr Pro Leu Tyr Glu Gln His Thr Leu Cys Gly Ala
1               5                   10                  15

Arg Met Val Asp Phe His Gly Trp Met Met Pro Leu His Tyr Gly Ser
            20                  25                  30

Gln Ile Asp Glu His His Ala Val Arg Thr Asp Ala Gly Met Phe Asp
        35                  40                  45

Val Ser His Met Thr Ile Val Asp Leu Arg Gly Ser Arg Thr Arg Glu
50                  55                  60

Phe Leu Arg Tyr Leu Leu Ala Asn Asp Val Ala Lys Leu Thr Lys Ser
65                  70                  75                  80

Gly Lys Ala Leu Tyr Ser Gly Met Leu Asn Ala Ser Gly Gly Val Ile
            85                  90                  95

Asp Asp Leu Ile Val Tyr Tyr Phe Thr Glu Asp Phe Phe Arg Leu Val
        100                 105                 110

Val Asn Ser Ala Thr Arg Glu Lys Asp Leu Ser Trp Ile Thr Gln His
    115                 120                 125

Ala Glu Pro Phe Gly Ile Glu Ile Thr Val Arg Asp Asp Leu Ser Met
130                 135                 140

Ile Ala Val Gln Gly Pro Asn Ala Gln Ala Lys Ala Ala Thr Leu Phe
145                 150                 155                 160

Asn Asp Ala Gln Arg Gln Ala Val Glu Gly Met Lys Pro Phe Phe Gly
                165                 170                 175

Val Gln Ala Gly Asp Leu Phe Ile Ala Thr Thr Gly Tyr Thr Gly Glu
            180                 185                 190

Ala Gly Tyr Glu Ile Ala Leu Pro Asn Glu Lys Ala Ala Asp Phe Trp
        195                 200                 205

Arg Ala Leu Val Glu Ala Gly Val Lys Pro Cys Gly Leu Gly Ala Arg
    210                 215                 220

Asp Thr Leu Arg Leu Glu Ala Gly Met Asn Leu Tyr Gly Gln Glu Met
225                 230                 235                 240

Asp Glu Thr Ile Ser Pro Leu Ala Ala Asn Met Gly Trp Thr Ile Ala
                245                 250                 255

Trp Glu Pro Ala Asp Arg Asp Phe Ile Gly Arg Glu Ala Leu Glu Val
            260                 265                 270

Gln Arg Glu His Gly Thr Glu Lys Leu Val Gly Leu Val Met Thr Glu
        275                 280                 285

Lys Gly Val Leu Arg Asn Glu Leu Pro Val Arg Phe Thr Asp Ala Gln
    290                 295                 300
```

```
Gly Asn Gln His Glu Gly Ile Ile Thr Ser Gly Thr Phe Ser Pro Thr
305                 310                 315                 320

Leu Gly Tyr Ser Ile Ala Leu Ala Arg Val Pro Glu Gly Ile Gly Glu
            325                 330                 335

Thr Ala Ile Val Gln Ile Arg Asn Arg Glu Met Pro Val Lys Val Thr
        340                 345                 350

Lys Pro Val Phe Val Arg Asn Gly Lys Ala Val Ala
        355                 360

<210> SEQ ID NO 47
<211> LENGTH: 390
<212> TYPE: DNA
<213> ORGANISM: Escherichia coli

<400> SEQUENCE: 47
atgagcaacg taccagcaga actgaaatac agcaaagaac acgaatggct gcgtaaagaa      60
gccgacggca cttacaccgt tggtattacc gaacatgctc aggagctgtt aggcgatatg     120
gtgtttgttg acctgccgga agtgggcgca acggttagcg cgggcgatga ctgcgcggtt     180
gccgaatcag taaaagcggc gtcagacatt tatgcgccag taagcggtga atcgtggcg      240 gtaaacgacg cactgagcga ttccccggaa ctggtgaaca gcgaaccgta tgcaggtggc     300
tggatcttta aaatcaaagc cagcgatgaa agcgaactgg aatcactgct ggatgcgacc     360
gcatacgaag cattgttaga agacgagtaa                                      390

<210> SEQ ID NO 48
<211> LENGTH: 129
<212> TYPE: PRT
<213> ORGANISM: Escherichia coli

<400> SEQUENCE: 48

Met Ser Asn Val Pro Ala Glu Leu Lys Tyr Ser Lys Glu His Glu Trp
1               5                   10                  15

Leu Arg Lys Glu Ala Asp Gly Thr Tyr Thr Val Gly Ile Thr Glu His
            20                  25                  30

Ala Gln Glu Leu Leu Gly Asp Met Val Phe Val Asp Leu Pro Glu Val
        35                  40                  45

Gly Ala Thr Val Ser Ala Gly Asp Asp Cys Ala Val Ala Glu Ser Val
    50                  55                  60

Lys Ala Ala Ser Asp Ile Tyr Ala Pro Val Ser Gly Glu Ile Val Ala
65                  70                  75                  80

Val Asn Asp Ala Leu Ser Asp Ser Pro Glu Leu Val Asn Ser Glu Pro
                85                  90                  95

Tyr Ala Gly Gly Trp Ile Phe Lys Ile Lys Ala Ser Asp Glu Ser Glu
            100                 105                 110

Leu Glu Ser Leu Leu Asp Ala Thr Ala Tyr Glu Ala Leu Leu Glu Asp
        115                 120                 125

Glu

<210> SEQ ID NO 49
<211> LENGTH: 2874
<212> TYPE: DNA
<213> ORGANISM: Escherichia coli

<400> SEQUENCE: 49
atgacacaga cgttaagcca gcttgaaaac agcggcgctt ttattgaacg ccatatcgga      60
```

```
ccggacgccg cgcaacagca agaaatgctg aatgccgttg gtgcacaatc gttaaacgcg      120
ctgaccggcc agattgtgcc gaaagatatt cagcttgcga ccccgccgca ggttggcgca      180
ccggcgaccg aatacgccgc actggcagaa ctcaaggcta ttgccagtcg caataaacgc      240
ttcacgtctt acatcggcat gggttacacc gccgtgcagc taccgccggt tatcctgcgt      300
aacatgctgg aaaatccggg ctggtatacc gcgtacactc cgtatcaacc tgaagtctcc      360
cagggccgcc ttgaagcact gctcaacttc agcaggtaa cgctggattt gactggactg      420
gatatggcct ctgcttctct tctggacgag gccaccgctg ccgccgaagc aatggcgatg      480
gcgaaacgcg tcagcaaact gaaaaatgcc aaccgcttct tcgtggcttc cgatgtgcat      540
ccgcaaacgc tggatgtggt ccgtactcgt gccgaaacct ttggttttga agtgattgtc      600
gatgacgcgc aaaaagtgct cgaccatcag gacgtcttcg gcgtgctgtt acagcaggtt      660
ggcacaaccg gtgaaatcca cgactacacc gcgcttatta gcgaactgaa atcacgcaaa      720
attgtggtca gcgttgccgc cgatattatg gcgctggtgc tgttaactgc gccgggtaaa      780
cagggcgcgg atattgtttt tggttcggcg caacgcttcg gcgtgccgat gggctacggt      840
ggcccacacg cggcattctt tgcggcgaaa gatgaataca aacgctcaat gccgggccgt      900
attatcggtg tatcgaaaga tgcagctggc aataccgcgc tgcgcatggc gatgcagact      960
cgcgagcaac atatccgccg tgagaaagcg aactccaaca tttgtacttc ccaggtactg     1020
ctggcaaaca tcgccagcct gtatgccgtt tatcacggcc cgattggcct gaaacgtatc     1080
gctaaccgca ttcaccgttt gaccgatatc ctggcggcag gcctgcaaca aaaaggtctg     1140
aagctgcgcg atgcgcacta tttcgacacc ttgtgtgtgg aagtggccga caaagcgggc     1200
gtactgacgc gtgccgaagc ggctgaaatc aacctgcgta gcgatattct gaacgcggtt     1260
gggatcaccc ttgatgaaac aaccacgcgt gaaaacgtaa tgcagctttt caacgtgctg     1320
ctgggcgata ccacggcct ggacatcgac acgctggaca agacgtggc tcacgacagc     1380 cgctctatcc agcctgcgat gctgcgcgac gacgaaatcc tcacccatcc ggtgtttaat     1440
cgctaccaca gcgaaaccga atgatgcgc tatatgcact cgctggagcg taaagatctg     1500
gcgctgaatc aggcgatgat cccgctgggt tcctgcacca tgaaactgaa cgccgccgcc     1560
gagatgatcc caatcacctg gccggaattt gccgaactgc acccgttttg tccgccggaa     1620
caggctgaag ttatcagca gatgattgcg cagctggctg actggctggt gaaactgacc     1680
ggttacgacg ccgtttgtat gcagccgaac tccggcgcac agggcgaata cgcgggcctg     1740
ctggcgattc gtcattatca tgaaagccgc aacgaaggc atcgcgatat ctgcctgatc     1800
ccggcttctg cgcacggaac taaccccgct tctgcacata tggcaggaat gcaggtggtg     1860
gttgtggcgt gtgataaaaa cggcaacatc gatctgactg atctgcgcgc gaaagcggaa     1920
caggcgggcg ataacctctc ctgtatcatg gtgacttatc cttctaccca cggcgtgtat     1980
gaagaaacga tccgtgaagt gtgtgaagtc gtgcatcagt tcggcggtca ggtttacctt     2040
gatggcgcga acatgaacgc ccaggttggc atcacctcgc cgggctttat tggcgcggac     2100
gtttcgcacc tcaacctgca taaaacttc tgcattccgc acggcggtgg tggtccgggt     2160
atgggaccga tcggtgtgaa agcgcatctg cacggttttg tacccgggtca tagcgtggtg     2220 caaatcgaag gcatgttaac ccgtcagggc gcagtttctg cggcaccgtt cggtagcgcc     2280
tctatcctgc caatcagctg gatgtacatc gcatgatgg gcgcagaagg gctgaaaaaa     2340
gcaagccagg tggcaatcct caacgccaac tatattgcca gccgcctgca ggatgccttc     2400
ccggtgctgt ataccggtcg cgacggtcgc gtggcgcacg aatgtattct cgatattcgc     2460
```

```
ccgctgaaag aagaaaccgg catcagcgag ctggatattg ccaagcgcct gatcgactac    2520
ggtttccacg cgccgaccat gtcgttcccg gtggcgggta cgctgatggt tgaaccgact    2580
gaatctgaaa gcaaagtgga actggatcgc tttatcgacg cgatgctggc tatccgcgca    2640
gaaatcgacc aggttaaagc cggtgtctgg ccgctggaag ataacccgct ggtgaacgcg    2700
ccgcacattc agaacgaact ggtcgccgag tgggcgcatc cgtacagccg tgaagttgca    2760
gtattcccgg caggtgtggc agacaaatac tggccgacgg tgaaacgtct ggatgatgtt    2820
tacggcgacc gtaacctgtt ctgctcctgc gtaccgatta gcgaatacca gtaa          2874
```

<210> SEQ ID NO 50
<211> LENGTH: 957
<212> TYPE: PRT
<213> ORGANISM: Escherichia coli

<400> SEQUENCE: 50

```
Met Thr Gln Thr Leu Ser Gln Leu Glu Asn Ser Gly Ala Phe Ile Glu
 1               5                  10                  15

Arg His Ile Gly Pro Asp Ala Ala Gln Gln Gln Glu Met Leu Asn Ala
             20                  25                  30

Val Gly Ala Gln Ser Leu Asn Ala Leu Thr Gly Gln Ile Val Pro Lys
         35                  40                  45

Asp Ile Gln Leu Ala Thr Pro Pro Gln Val Gly Ala Pro Ala Thr Glu
     50                  55                  60

Tyr Ala Ala Leu Ala Glu Leu Lys Ala Ile Ala Ser Arg Asn Lys Arg
 65                  70                  75                  80

Phe Thr Ser Tyr Ile Gly Met Gly Tyr Thr Ala Val Gln Leu Pro Pro
                 85                  90                  95

Val Ile Leu Arg Asn Met Leu Glu Asn Pro Gly Trp Tyr Thr Ala Tyr
            100                 105                 110

Thr Pro Tyr Gln Pro Glu Val Ser Gln Gly Arg Leu Glu Ala Leu Leu
        115                 120                 125

Asn Phe Gln Gln Val Thr Leu Asp Leu Thr Gly Leu Asp Met Ala Ser
    130                 135                 140

Ala Ser Leu Leu Asp Glu Ala Thr Ala Ala Ala Glu Ala Met Ala Met
145                 150                 155                 160

Ala Lys Arg Val Ser Lys Leu Lys Asn Ala Asn Arg Phe Phe Val Ala
                165                 170                 175

Ser Asp Val His Pro Gln Thr Leu Asp Val Val Arg Thr Arg Ala Glu
            180                 185                 190

Thr Phe Gly Phe Glu Val Ile Val Asp Asp Ala Gln Lys Val Leu Asp
        195                 200                 205

His Gln Asp Val Phe Gly Val Leu Leu Gln Gln Val Gly Thr Thr Gly
    210                 215                 220

Glu Ile His Asp Tyr Thr Ala Leu Ile Ser Glu Leu Lys Ser Arg Lys
225                 230                 235                 240

Ile Val Val Ser Val Ala Ala Asp Ile Met Ala Leu Val Leu Leu Thr
                245                 250                 255

Ala Pro Gly Lys Gln Gly Ala Asp Ile Val Phe Gly Ser Ala Gln Arg
            260                 265                 270

Phe Gly Val Pro Met Gly Tyr Gly Gly Pro His Ala Ala Phe Phe Ala
        275                 280                 285

Ala Lys Asp Glu Tyr Lys Arg Ser Met Pro Gly Arg Ile Ile Gly Val
    290                 295                 300
```

```
Ser Lys Asp Ala Ala Gly Asn Thr Ala Leu Arg Met Ala Met Gln Thr
305                 310                 315                 320

Arg Glu Gln His Ile Arg Arg Glu Lys Ala Asn Ser Asn Ile Cys Thr
            325                 330                 335

Ser Gln Val Leu Leu Ala Asn Ile Ala Ser Leu Tyr Ala Val Tyr His
            340                 345                 350

Gly Pro Ile Gly Leu Lys Arg Ile Ala Asn Arg Ile His Arg Leu Thr
            355                 360                 365

Asp Ile Leu Ala Ala Gly Leu Gln Gln Lys Gly Leu Lys Leu Arg His
370                 375                 380

Ala His Tyr Phe Asp Thr Leu Cys Val Glu Val Ala Asp Lys Ala Gly
385                 390                 395                 400

Val Leu Thr Arg Ala Glu Ala Glu Ile Asn Leu Arg Ser Asp Ile
                405                 410                 415

Leu Asn Ala Val Gly Ile Thr Leu Asp Glu Thr Thr Arg Glu Asn
                420                 425                 430

Val Met Gln Leu Phe Asn Val Leu Leu Gly Asp Asn His Gly Leu Asp
            435                 440                 445

Ile Asp Thr Leu Asp Lys Asp Val Ala His Asp Ser Arg Ser Ile Gln
            450                 455                 460

Pro Ala Met Leu Arg Asp Asp Glu Ile Leu Thr His Pro Val Phe Asn
465                 470                 475                 480

Arg Tyr His Ser Glu Thr Glu Met Met Arg Tyr Met His Ser Leu Glu
                485                 490                 495

Arg Lys Asp Leu Ala Leu Asn Gln Ala Met Ile Pro Leu Gly Ser Cys
            500                 505                 510

Thr Met Lys Leu Asn Ala Ala Ala Glu Met Ile Pro Ile Thr Trp Pro
            515                 520                 525

Glu Phe Ala Glu Leu His Pro Phe Cys Pro Pro Glu Gln Ala Glu Gly
            530                 535                 540

Tyr Gln Gln Met Ile Ala Gln Leu Ala Asp Trp Leu Val Lys Leu Thr
545                 550                 555                 560

Gly Tyr Asp Ala Val Cys Met Gln Pro Asn Ser Gly Ala Gln Gly Glu
                565                 570                 575

Tyr Ala Gly Leu Leu Ala Ile Arg His Tyr His Glu Ser Arg Asn Glu
                580                 585                 590

Gly His Arg Asp Ile Cys Leu Ile Pro Ala Ser Ala His Gly Thr Asn
            595                 600                 605

Pro Ala Ser Ala His Met Ala Gly Met Gln Val Val Val Ala Cys
610                 615                 620

Asp Lys Asn Gly Asn Ile Asp Leu Thr Asp Leu Arg Ala Lys Ala Glu
625                 630                 635                 640

Gln Ala Gly Asp Asn Leu Ser Cys Ile Met Val Thr Tyr Pro Ser Thr
                645                 650                 655

His Gly Val Tyr Glu Glu Thr Ile Arg Glu Val Cys Glu Val Val His
            660                 665                 670

Gln Phe Gly Gly Gln Val Tyr Leu Asp Gly Ala Asn Met Asn Ala Gln
            675                 680                 685

Val Gly Ile Thr Ser Pro Gly Phe Ile Gly Ala Asp Val Ser His Leu
            690                 695                 700

Asn Leu His Lys Thr Phe Cys Ile Pro His Gly Gly Gly Gly Pro Gly
705                 710                 715                 720
```

Met Gly Pro Ile Gly Val Lys Ala His Leu Ala Pro Phe Val Pro Gly
            725                 730                 735

His Ser Val Val Gln Ile Glu Gly Met Leu Thr Arg Gln Gly Ala Val
            740                 745                 750

Ser Ala Ala Pro Phe Gly Ser Ala Ser Ile Leu Pro Ile Ser Trp Met
            755                 760                 765

Tyr Ile Arg Met Met Gly Ala Glu Gly Leu Lys Lys Ala Ser Gln Val
            770                 775                 780

Ala Ile Leu Asn Ala Asn Tyr Ile Ala Ser Arg Leu Gln Asp Ala Phe
785                 790                 795                 800

Pro Val Leu Tyr Thr Gly Arg Asp Gly Arg Val Ala His Glu Cys Ile
                    805                 810                 815

Leu Asp Ile Arg Pro Leu Lys Glu Glu Thr Gly Ile Ser Glu Leu Asp
                    820                 825                 830

Ile Ala Lys Arg Leu Ile Asp Tyr Gly Phe His Ala Pro Thr Met Ser
                    835                 840                 845

Phe Pro Val Ala Gly Thr Leu Met Val Glu Pro Thr Glu Ser Glu Ser
            850                 855                 860

Lys Val Glu Leu Asp Arg Phe Ile Asp Ala Met Leu Ala Ile Arg Ala
865                 870                 875                 880

Glu Ile Asp Gln Val Lys Ala Gly Val Trp Pro Leu Glu Asp Asn Pro
                    885                 890                 895

Leu Val Asn Ala Pro His Ile Gln Asn Glu Leu Val Ala Glu Trp Ala
            900                 905                 910

His Pro Tyr Ser Arg Glu Val Ala Val Phe Pro Ala Gly Val Ala Asp
            915                 920                 925

Lys Tyr Trp Pro Thr Val Lys Arg Leu Asp Asp Val Tyr Gly Asp Arg
930                 935                 940

Asn Leu Phe Cys Ser Cys Val Pro Ile Ser Glu Tyr Gln
945                 950                 955

<210> SEQ ID NO 51
<211> LENGTH: 4543
<212> TYPE: DNA
<213> ORGANISM: Escherichia coli

<400> SEQUENCE: 51

| | | | | |
|---|---|---|---|---|
| atatacatat | ggcacaacag | actcctttgt | acgaacaaca | cacgctttgc | ggcgctcgca | 60 |
| tggtggattt | ccacggctgg | atgatgccgc | tgcattacgg | ttcgcaaatc | gacgaacatc | 120 |
| atgcggtacg | taccgatgcc | ggaatgtttg | atgtgtcaca | tatgaccatc | gtcgatctcc | 180 |
| gcggcagccg | cacccgggag | tttctgcgtt | atctgctggc | gaacgatgtg | gcgaagctca | 240 |
| ccaaaagcgg | caaagccctt | actcggggga | tgttgaatgc | ctctggcggt | gtgatagatg | 300 |
| acctcatcgt | ctactacttt | actgaagatt | tcttccgcct | cgttgttaac | tccgccaccc | 360 |
| gcgaaaaaga | cctctcctgg | attacccaac | acgctgaacc | tttcggcatc | gaaattaccg | 420 |
| ttcgtgatga | ccttttccatg | attgccgtgc | aagggccgaa | tgcgcaggca | aaagctgcca | 480 |
| cactgtttaa | tgacgcccag | cgtcaggcgg | tggaagggat | gaaaccgttc | tttggcgtgc | 540 |
| aggcgggcga | tctgttttat | gccaccactg | gttataccgg | tgaagcgggc | tatgaaattg | 600 |
| cgctgcccaa | tgaaaaagcg | gccgatttct | ggcgtgcgct | ggtggaagcg | ggtgttaagc | 660 |
| catgtggctt | gggcgcgcgt | gacacgctgc | gtctggaagc | gggcatgaat | ctttatggtc | 720 |
| aggagatgga | cgaaactatt | tctcctttag | ccgccaacat | gggctggact | atcgcctggg | 780 |

```
aaccggcaga tcgtgacttt atcggtcgtg aagccctgga agtgcagcgt gagcatggta    840
cagaaaaact ggttggtctg gtgatgaccg aaaaaggcgt gctgcgtaat gaactgccgg    900
tacgctttac cgatgcgcag ggcaaccagc atgaaggcat tatcaccagc ggtactttct    960
ccccgacgct gggttacagc attgcgctgg cgcgcgtgcc ggaaggtatt ggcgaaacgg   1020
cgattgtgca aattcgcaac cgtgaaatgc cggttaaagt gacaaaacct gttttgtgc    1080
gtaacggcaa agccgtcgcg tgatttactt ttttggagat tgattgatga gcaacgtacc   1140
agcagaactg aaatacagca agaacacga atggctgcgt aaagaagccg acggcactta    1200
caccgttggt attaccgaac atgctcagga gctgttaggc gatatggtgt tgttgacct    1260
gccggaagtg ggcgcaacgg ttagcgcggg cgatgactgc gcggttgccg aatcagtaaa   1320
agcggcgtca gacatttatg cgccagtaag cggtgaaatc gtggcggtaa acgacgcact   1380
gagcgattcc ccggaactgg tgaacagcga accgtatgca ggtggctgga tcttaaaat    1440
caaagccagc gatgaaagcg aactggaatc actgctggat gcgaccgcat acgaagcatt   1500
gttagaagac gagtaacggc tttattcctc ttctgcggga gaggatcagg gtgaggaaaa   1560
tttatgcctc accctcactc tcttcgtaag gagagaggtt cacaattcac tgcacgtttc   1620
aggaaccatc gctcatgaca cagacgttaa gccagcttga aaacagcggc gcttttattg   1680
aacgccatat cggaccggac gccgcgcaac agcaagaaat gctgaatgcc gttggtgcac   1740
aatcgttaaa cgcgctgacc ggccagattg tgccgaaaga tattcagctt gcgaccccgc   1800
cgcaggttgg cgcaccggcg accgaatacg ccgcactggc agaactcaag gctattgcca   1860
gtcgcaataa acgcttcacg tcttacatcg gcatgggtta caccgccgtg cagctaccgc   1920
cggttatcct gcgtaacatg ctggaaaatc cgggctggta taccgcgtac actccgtatc   1980
aacctgaagt ctcccagggc cgccttgaag cactgctcaa cttccagcag gtaacgctgg   2040
atttgactgg actggatatg cctctgcttt ctcttctgga cgaggccacc gctgccgccg   2100
aagcaatggc gatggcgaaa cgcgtcagca aactgaaaaa tgccaaccgc ttcttcgtgg   2160
cttccgatgt gcatccgcaa acgctggatg tggtccgtac tcgtgccgaa acctttggtt   2220
ttgaagtgat tgtcgatgac gcgcaaaaag tgctcgacca tcaggacgtc ttcggcgtgc   2280
tgttacagca ggttggcaca accggtgaaa tccacgacta caccgcgctt attagcgaac   2340
tgaaatcacg caaaattgtg gtcagcgttg ccgccgatat tatggcgctg gtgctgttaa   2400
ctgcgccggg taaacagggc gcggatattg ttttggttc ggcgcaacgc ttcggcgtgc    2460
cgatgggcta cggtggccca cacgcggcat tcttgcggc gaaagatgaa tacaaacgct    2520
caatgccggg ccgtattatc ggtgtatcga aagatgcagc tggcaatacc gcgctgcgca   2580
tggcgatgca gactcgcgag caacatatcc gccgtgagaa agcgaactcc aacatttgta   2640
cttcccaggt actgctggca aacatcgcca gcctgtatgc cgtttatcac ggcccgattg   2700
gcctgaaacg tatcgctaac cgcattcacc gtttgaccga tatcctggcg gcaggcctgc   2760
aacaaaaagg tctgaagctg cgccatgcgc actatttcga caccttgtgt gtggaagtgg   2820
ccgacaaagc gggcgtactg acgcgtgccg aagcggctga atcaacctg cgtagcgata    2880
ttctgaacgc ggttgggatc acccttgatg aaacaaccac gcgtgaaaac gtaatgcagc   2940
ttttcaacgt gctgctgggc gataaccacg gcctggacat cgacacgctg gacaaagacg   3000
tggctcacga cagccgctct atccagcctg cgatgctgcg cgacgacgaa atcctcaccc   3060
atccggtgtt taatcgctac cacagcgaaa ccgaaatgat gcgctatatg cactcgctgg   3120
agcgtaaaga tctggcgctg aatcaggcga tgatcccgct gggttcctgc accatgaaac   3180
```

```
tgaacgccgc cgccgagatg atcccaatca cctggccgga atttgccgaa ctgcacccgt    3240
tttgtccgcc ggaacaggct gaaggttatc agcagatgat tgcgcagctg gctgactggc    3300
tggtgaaact gaccggttac gacgccgttt gtatgcagcc gaactccggc gcacagggcg    3360
aatacgcggg cctgctggcg attcgtcatt atcatgaaag ccgcaacgaa gggcatcgcg    3420
atatctgcct gatcccggct tctgcgcacg gaactaaccc cgcttctgca catatggcag    3480
gaatgcaggt ggtggttgtg gcgtgtgata aaaacggcaa catcgatctg actgatctgc    3540
gcgcgaaagc ggaacaggcg ggcgataacc tctcctgtat catggtgact tatccttcta    3600
cccacggcgt gtatgaagaa cgatccgtg aagtgtgtga agtcgtgcat cagttcggcg     3660
gtcaggttta ccttgatggc gcgaacatga acgcccaggt tggcatcacc tcgccgggct    3720
ttattggcgc ggacgtttcg cacctcaacc tgcataaaac tttctgcatt ccgcacggcg    3780
gtggtggtcc gggtatggga ccgatcggtg tgaaagcgca tctggcaccg tttgtaccgg    3840
gtcatagcgt ggtgcaaatc gaaggcatgt taacccgtca gggcgcagtt tctgcggcac    3900
cgttcggtag cgcctctatc ctgccaatca gctggatgta catccgcatg atgggcgcag    3960
aagggctgaa aaaagcaagc caggtggcaa tcctcaacgc caactatatt gccagccgcc    4020
tgcaggatgc cttcccggtg ctgtataccg tcgcgacgg tcgcgtggcg cacgaatgta    4080
ttctcgatat tcgcccgctg aaagaagaaa ccggcatcag cgagctggat attgccaagc    4140
gcctgatcga ctacggtttc cacgcgccga ccatgtcgtt cccggtggcg ggtacgctga    4200
tggttgaacc gactgaatct gaaagcaaag tggaactgga tcgctttatc gacgcgatgc    4260
tggctatccg cgcagaaatc gaccaggtta agccggtgt ctggccgctg aagataacc     4320 cgctggtgaa cgcgccgcac attcagaacg aactggtcgc cgagtgggcg catccgtaca    4380
gccgtgaagt tgcagtattc ccggcaggtg tggcagacaa atactggccg acggtgaaac    4440
gtctggatga tgtttacggc gaccgtaacc tgttctgctc ctgcgtaccg attagcgaat    4500
accagtaatt cactgattcg actatcttct aaaggcgctt cgg                     4543
```

<210> SEQ ID NO 52
<211> LENGTH: 8433
<212> TYPE: DNA
<213> ORGANISM: Artificial
<220> FEATURE:
<223> OTHER INFORMATION: Vector

<400> SEQUENCE: 52

```
cgataagctt cgactgcacg gtgcaccaat gcttctggcg tcaggcagcc atcggaagct      60
gtggtatggc tgtgcaggtc gtaaatcact gcataattcg tgtcgctcaa ggcgcactcc     120
cgttctggat aatgttttt gcgccgacat cataacggtt ctggcaaata ttctgaaatg     180
agctgttgac aattaatcat ccggctcgta taatgtgtgg aattgtgagc ggataacaat    240
ttcagaattc aaaagatctt ttaagaagga gatatacata tggcacaaca gactcctttg    300
tacgaacaac acacgctttg cggcgctcgc atggtggatt ccacggctg atgatgccg      360 ctgcattacg gttcgcaaat cgacgaacat catgcggtac gtaccgatgc cggaatgttt    420
gatgtgtcac atatgaccat cgtcgatctc cgcggcagcc gcacccggga gtttctgcgt    480
tatctgctgg cgaacgatgt ggcgaagctc accaaaagcg gcaaagccct ttactcgggg    540
atgttgaatg cctctggcgg tgtgatagat gacctcatcg tctactactt tactgaagat    600
ttcttccgcc tcgttgttaa ctccgccacc cgcgaaaaag acctctcctg gattacccaa    660
```

```
cacgctgaac ctttcggcat cgaaattacc gttcgtgatg acctttccat gattgccgtg      720
caagggccga atgcgcaggc aaaagctgcc acactgttta atgacgccca gcgtcaggcg      780
gtggaaggga tgaaaccgtt ctttggcgtg caggcgggcg atctgtttat tgccaccact      840
ggttataccg gtgaagcggg ctatgaaatt cgctgcccca tgaaaaagc ggccgatttc       900 tggcgtgcgc tggtggaagc gggtgttaag ccatgtggct gggcgcgcg tgacacgctg       960 cgtctggaag cgggcatgaa tctttatggt caggagatgg acgaaactat ttctcctta     1020 gccgccaaca tgggctggac tatcgcctgg gaaccggcag atcgtgactt tatcggtcgt     1080
gaagccctgg aagtgcagcg tgagcatggt acagaaaaac tggttggtct ggtgatgacc     1140
gaaaaaggcg tgctgcgtaa tgaactgccg gtacgcttta ccgatgcgca gggcaaccag     1200
catgaaggca ttatcaccag cggtactttc tccccgacgc tgggttacag cattgcgctg     1260
gcgcgcgtgc cggaaggtat tggcgaaacg gcgattgtgc aaattcgcaa ccgtgaaatg     1320
ccggttaaag tgacaaaacc tgttttttgtg cgtaacggca agccgtcgc gtgatttact     1380 ttttggaga ttgattgatg agcaacgtac cagcagaact gaaatacagc aaagaacacg      1440
aatggctgcg taaagaagcc gacggcactt acaccgttgg tattaccgaa catgctcagg     1500
agctgttagg cgatatggtg tttgttgacc tgccggaagt gggcgcaacg gttagcgcgg     1560
gcgatgactg cgcggttgcc gaatcagtaa aagcggcgtc agacatttat gcgccagtaa     1620
gcggtgaaat cgtggcggta acgacgcac tgagcgattc cccggaactg gtgaacagcg      1680
aaccgtatgc aggtggctgg atctttaaaa tcaaagccag cgatgaaagc gaactggaat     1740
cactgctgga tgcgaccgca tacgaagcat tgttagaaga cgagtaacgg ctttattcct     1800
cttctgcggg agaggatcag ggtgaggaaa atttatgcct caccctcact ctcttcgtaa     1860
ggagagaggt tcacaattca ctgcacgttt caggaaccat cgctcatgac acagacgtta     1920
agccagcttg aaaacagcgg cgcttttatt gaacgccata tcggaccgga cgccgcgcaa     1980
cagcaagaaa tgctgaatgc cgttggtgca caatcgttaa acgcgctgac cggccagatt     2040
gtgccgaaag atattcagct tgcgaccccg ccgcaggttg gcgcaccggc gaccgaatac     2100
gccgcactgg cagaactcaa ggctattgcc agtcgcaata aacgcttcac gtcttacatc     2160
ggcatgggtt acaccgccgt gcagctaccg ccggttatcc tgcgtaacat gctggaaaat     2220
ccgggctggt ataccgcgta cactccgtat caacctgaag tctcccaggg ccgccttgaa     2280
gcactgctca acttccagca ggtaacgctg gatttgactg gactggatat ggcctctgct     2340
tctcttctgg acgaggccac cgctgccgcc gaagcaatgg cgatgcgaa acgcgtcagc      2400 aaactgaaaa atgccaaccg cttcttcgtg gcttccgatg tgcatccgca aacgctggat     2460
gtggtccgta ctcgtgccga aacctttggt tttgaagtga ttgtcgatga cgcgcaaaaa     2520
gtgctcgacc atcaggacgt cttcggcgtg ctgttacagc aggttggcac aaccggtgaa     2580
atccacgact acaccgcgct tattagcgaa ctgaaatcac gcaaaattgt ggtcagcgtt     2640
gccgccgata ttatggcgct ggtgctgtta actgcgccgg gtaaacaggg cgcggatatt     2700 gttttttggtt cggcgcaacg cttcggcgtg ccgatgggct acggtggccc acacgcggca     2760
ttctttgcgg cgaaagatga atacaaacgc tcaatgccgg ccgtattat cggtgtatcg     2820 aaagatgcag ctggcaatac cgcgctgcgc atggcgatgc agactcgcga gcaacatatc     2880
cgccgtgaga aagcgaactc caacatttgt acttcccagg tactgctggc aaacatcgcc     2940
agcctgtatg ccgtttatca cggcccgatt ggcctgaaac gtatcgctaa ccgcattcac     3000
cgtttgaccg atatcctggc ggcaggcctg caacaaaaag gtctgaagct gcgccatgcg     3060
```

```
cactatttcg acaccttgtg tgtggaagtg gccgacaaag cgggcgtact gacgcgtgcc    3120
gaagcggctg aaatcaacct gcgtagcgat attctgaacg cggttgggat caccettgat    3180 gaaacaacca cgcgtgaaaa cgtaatgcag cttttcaacg tgctgctggg cgataaccac    3240
ggcctggaca tcgacacgct ggacaaagac gtggctcacg acagccgctc tatccagcct    3300
gcgatgctgc gcgacgacga aatcctcacc catccggtgt ttaatcgcta ccacagcgaa    3360
accgaaatga tgcgctatat gcactcgctg agcgtaaaag atctggcgct gaatcaggcg    3420
atgatcccgc tgggttcctg caccatgaaa ctgaacgccg ccgccgagat gatcccaatc    3480
acctggccga aatttgccga actgcacccg ttttgtccgc cggaacaggc tgaaggttat    3540
cagcagatga ttgcgcagct ggctgactgg ctggtgaaac tgaccggtta cgacgccgtt    3600
tgtatgcagc cgaactccgg cgcacagggc gaatacgcgg gcctgctggc gattcgtcat    3660
tatcatgaaa gccgcaacga agggcatcgc gatatctgcc tgatcccggc ttctgcgcac    3720
ggaactaacc ccgcttctgc acatatggca ggaatgcagg tggtggttgt ggcgtgtgat    3780
aaaaacggca acatcgatct gactgatctg cgcgcgaaag cggaacaggc gggcgataac    3840
ctctcctgta tcatggtgac ttatccttct acccacggcg tgtatgaaga aacgatccgt    3900
gaagtgtgtg aagtcgtgca tcagttcggc ggtcaggttt accttgatgg cgcgaacatg    3960
aacgcccagg ttggcatcac ctcgccgggc tttattggcg cggacgtttc gcacctcaac    4020
ctgcataaaa cttctgcat tccgcacggc ggtggtggtc cgggtatggg accgatcggt    4080
gtgaaagcgc atctggcacc gtttgtaccg ggtcatagcg tggtgcaaat cgaaggcatg    4140
ttaacccgtc agggcgcagt ttctgcggca ccgttcggta gcgcctctat cctgccaatc    4200
agctggatgt acatccgcat gatgggcgca gaagggctga aaaagcaag ccaggtggca    4260 atcctcaacg ccaactatat tgccagccgc ctgcaggatg ccttcccggt gctgtatacc    4320
ggtcgcgacg tcgcgtggc gcacgaatgt attctcgata ttcgcccgct gaaagaagaa    4380
accggcatca gcgagctgga tattgccaag cgcctgatcg actacggttt ccacgcgccg    4440
accatgtcgt tcccggtggc gggtacgctg atggttgaac cgactgaatc tgaaagcaaa    4500
gtggaactgg atcgctttat cgacgcgatg ctggctatcc gcgcagaaat cgaccaggtt    4560
aaagccggtg tctggccgct ggaagataac ccgctggtga acgcgccgca cattcagaac    4620
gaactggtcg ccgagtgggc gcatccgtac agccgtgaag ttgcagtatt cccggcaggt    4680
gtggcagaca atactggcc gacggtgaaa cgtctggatg atgtttacgg cgaccgtaac    4740
ctgttctgct cctgcgtacc gattagcgaa taccagtaat tcactgattc gactatcttc    4800
taaaggcgct tcgggtcgac cgatgcccttgagagccttc aacccagtca gctccttccg    4860
gtgggcgcgg gcatgactat cgtcgccgc acttatgact gtcttcttta tcatgcaact    4920
cgtaggacag gtgccggcag cgctctgggt cattttcggc gaggaccgct ttcgctggag    4980
cgcgacgatg atcggcctgt cgcttgcggt attcggaatc ttgcacgccc tcgctcaagc    5040
cttcgtcact ggtcccgcca ccaaacgttt cggcgagaag caggccatta tcgccggcat    5100
ggcggccgac gcgctgggct acgtcttgct ggcgttcgcg acgcgaggct ggatggcctt    5160
ccccattatg attcttctcg cttccggcgg catcgggatg cccgcgttgc aggccatgct    5220
gtccaggcag gtagatgacg accatcaggg acagcttcaa ggatcgctcg cggctcttac    5280
cagcctaact tcgatcactg gaccgctgat cgtcacggcg atttatgccg cctcggcgag    5340
cacatggaac gggttggcat ggattgtagg cgccgcccta taccttgtct gcctccccgc    5400
```

```
gttgcgtcgc ggtgcatgga gccgggccac ctcgacctga atggaagccg gcggcacctc   5460
gctaacggat tcaccactcc aagaattgga gccaatcaat tcttgcggag aactgtgaat   5520
gcgcaaacca acccttggca gaacatatcc atcgcgtccg ccatctccag cagccgcacg   5580
cggcgcatct cgggcagcgt tgggtcctgg ccacgggtgc gcatgatcgt gctcctgtcg   5640
ttgaggaccc ggctaggctg gcggggttgc cttactggtt agcagaatga atcaccgata   5700
cgcgagcgaa cgtgaagcga ctgctgctgc aaaacgtctg cgacctgagc aacaacatga   5760
atggtcttcg gtttccgtgt tcgtaaagt ctggaaacgc ggaagtcccc tacgtgctgc   5820
tgaagttgcc cgcaacagag agtggaacca accggtgata ccgatact atgactgaga   5880 gtcaacgcca tgagcggcct catttcttat tctgagttac aacagtccgc accgctgtcc   5940
ggtagctcct tccggtgggc gcggggcatg actatcgtcg ccgcacttat gactgtcttc   6000
tttatcatgc aactcgtagg acaggtgccg gcagcgccca acagtccccc ggccacgggg   6060
cctgccacca tacccacgcc gaaacaagcg ccctgcacca ttatgttccg gatctgcatc   6120
gcaggatgct gctggctacc ctgtggaaca cctacatctg tattaacgaa gcgctaaccg   6180 ttttatcag gctctgggag gcagaataaa tgatcatatc gtcaattatt acctccacgg   6240
ggagagcctg agcaaactgg cctcaggcat ttgagaagca cacggtcaca ctgcttccgg   6300
tagtcaataa accggtaaac cagcaataga cataagcggc tatttaacga ccctgccctg   6360
aaccgacgac cgggtcgaat ttgctttcga atttctgcca ttcatccgct tattatcact   6420
tattcaggcg tagcaccagg cgtttaaggg caccaataac tgccttaaaa aaattacgcc   6480
ccgccctgcc actcatcgca gtactgttgt aattcattaa gcattctgcc gacatggaag   6540
ccatcacaga cggcatgatg aacctgaatc gccagcggca tcagcacctt gtcgccttgc   6600
gtataatatt tgcccatggt gaaaacgggg gcgaagaagt tgtccatatt ggccacgttt   6660
aaatcaaaac tggtgaaact cacccaggga ttggctgaga cgaaaaacat attctcaata   6720
aaccctttag ggaaataggc caggttttca ccgtaacacg ccacatcttg cgaatatatg   6780
tgtagaaact gccggaaatc gtcgtggtat tcactccaga gcgatgaaaa cgtttcagtt   6840
tgctcatgga aaacggtgta acaagggtga acactatccc atatcaccag ctcaccgtct   6900 tcattgcca tacggaattc cggatgagca ttcatcaggc gggcaagaat gtgaataaag   6960
gccggataaa acttgtgctt attttttcttt acggtctta aaaaggccgt aatatccagc   7020
tgaacggtct ggttataggt acattgagca actgactgaa atgcctcaaa atgttcttta   7080
cgatgccatt gggatatatc aacgtggta tatccagtga ttttttttctc cattttagct   7140 tccttagctc ctgaaaatct cgataactca aaaaatacgc ccggtagtga tcttatttca   7200
ttatggtgaa agttgaacc tcttacgtgc cgatcaacgt ctcattttcg ccaaaagttg   7260
gcccagggct tcccggtatc aacagggaca ccaggattta tttattctgc gaagtgatct   7320
tccgtcacag gtatttattc ggcgcaaagt gcgtcgggtg atgctgccaa cttactgatt   7380
tagtgtatga tggtgttttt gaggtgctcc agtggcttct gtttctatca gctgtccctc   7440
ctgttcagct actgacgggg tggtgcgtaa cggcaaaagc accgccggac atcagcgcta   7500
gcggagtgta tactggctta ctatgttggc actgatgagg gtgtcagtga agtgcttcat   7560
gtggcaggag aaaaaaggct gcaccggtgc gtcagcagaa tatgtgatac aggatatatt   7620
ccgcttcctc gctcactgac tcgctacgct cggtcgttcg actgcggcga gcggaaatgg   7680
cttacgaacg gggcggagat tcctggaag atgccaggaa gatacttaac agggaagtga   7740
gagggccgcg gcaaagccgt ttttccatag gctccgcccc cctgacaagc atcacgaaat   7800
```

```
ctgacgctca aatcagtggt ggcgaaaccc gacaggacta taaagatacc aggcgtttcc    7860
ccctggcggc tccctcgtgc gctctcctgt tcctgccttt cggtttaccg gtgtcattcc    7920
gctgttatgg ccgcgtttgt ctcattccac gcctgacact cagttccggg taggcagttc    7980
gctccaagct ggactgtatg cacgaacccc ccgttcagtc cgaccgctgc gccttatccg    8040
gtaactatcg tcttgagtcc aacccggaaa gacatgcaaa agcaccactg gcagcagcca    8100
ctggtaattg atttagagga gttagtcttg aagtcatgcg ccggttaagg ctaaactgaa    8160
aggacaagtt ttggtgactg cgctcctcca agccagttac ctcggttcaa agagttggta    8220
gctcagagaa cctccgaaaa accgcccctgc aaggcggttt tttcgttttc agagcaagag    8280
attacgcgca gaccaaaacg atctcaagaa gatcatctta ttaatcagat aaaatatttc    8340
tagatttcag tgcaatttat ctcttcaaat gtagcacctg aagtcagccc catacgatat    8400
aagttgtaat tctcatgttt gacagcttat cat                                 8433

<210> SEQ ID NO 53
<211> LENGTH: 35
<212> TYPE: DNA
<213> ORGANISM: Artificial
<220> FEATURE:
<223> OTHER INFORMATION: Primer

<400> SEQUENCE: 53
gaaggagata tacatatggc acaacagact ccttt                               35

<210> SEQ ID NO 54
<211> LENGTH: 36
<212> TYPE: DNA
<213> ORGANISM: Artificial
<220> FEATURE:
<223> OTHER INFORMATION: Primer

<400> SEQUENCE: 54
aagggcatcg gtcgacccga agcgccttta gaagat                              36

<210> SEQ ID NO 55
<211> LENGTH: 285
<212> TYPE: DNA
<213> ORGANISM: Artificial
<220> FEATURE:
<223> OTHER INFORMATION: Promoter

<400> SEQUENCE: 55
tatcatcgat aagcttcgac tgcacggtgc accaatgctt ctggcgtcag gcagccatcg    60
gaagctgtgg tatggctgtg caggtcgtaa atcactgcat aattcgtgtc gctcaaggcg   120
cactcccgtt ctggataatg tttttgcgc cgacatcata acggtctgg caaatattct    180 gaaatgagct gttgacaatt aatcatccgg ctcgtataat gtgtggaatt gtgagcggat   240
aacaatttca gaattcaaaa gatcttttaa gaaggagata tacat                   285

<210> SEQ ID NO 56
<211> LENGTH: 3898
<212> TYPE: DNA
<213> ORGANISM: Artificial
<220> FEATURE:
<223> OTHER INFORMATION: Vector

<400> SEQUENCE: 56
gaattccgga tgagcattca tcaggcgggc aagaatgtga ataaaggccg gataaaactt    60
```

```
gtgcttattt ttctttacgg tctttaaaaa ggccgtaata tccagctgaa cggtctggtt      120
ataggtacat tgagcaactg actgaaatgc ctcaaaatgt tctttacgat gccattggga      180
tatatcaacg gtggtatatc cagtgatttt tttctccatt ttagcttcct tagctcctga      240
aaatctcgat aactcaaaaa atacgcccgg tagtgatctt atttcattat ggtgaaagtt      300
ggaacctctt acgtgccgat caacgtctca ttttcgccaa aagttggccc agggcttccc      360
ggtatcaaca gggacaccag gatttattta ttctgcgaag tgatcttccg tcacaggtat      420
ttattcggcg caaagtgcgt cgggtgatgc tgccaactta ctgatttagt gtatgatggt      480 gttttttgagg tgctccagtg gcttctgttt ctatcagctg tccctcctgt tcagctactg      540
acggggtggt gcgtaacggc aaaagcaccg ccggacatca gcgctagcgg agtgtatact      600
ggcttactat gttggcactg atgagggtgt cagtgaagtg cttcatgtgg caggagaaaa      660
aaggctgcac cggtgcgtca gcagaatatg tgatacagga tatattccgc ttcctcgctc      720
actgactcgc tacgctcggt cgttcgactg cggcgagcgg aaatggctta cgaacggggc      780
ggagatttcc tggaagatgc caggaagata cttaacaggg aagtgagagg gccgcggcaa      840
agccgttttt ccataggctc cgccccctg acaagcatca cgaaatctga cgctcaaatc      900
agtggtggcg aaacccgaca ggactataaa gataccaggc gtttccccct ggcggctccc      960
tcgtgcgctc tcctgttcct gcctttcggt ttaccggtgt cattccgctg ttatggccgc     1020
gtttgtctca ttccacgcct gacactcagt tcccgggtagg cagttcgctc caagctggac     1080
tgtatgcacg aacccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta gcgcgagacc     1380
aaaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttc gactgcacgg tgcaccaatg cttctggcgt     1560
caggcagcca tcggaagctg tggtatggct gtgcaggtcg taaatcactg cataattcgt     1620
gtcgctcaag gcgcactccc gttctggata atgttttttg cgccgacatc ataacggttc     1680
tggcaaatat tctgaaatga ctgttgaca attaatcatc cggctcgtat aatgtgtgga     1740
attgtgagcg gataacaatt tcagaattca aaagatcttt taagaaggag atatacatgt     1800
cgaccgatgc ccttgagagc cttcaaccca gtcagctcct tccggtgggc gcggggcatg     1860
actatcgtcg ccgcacttat gactgtcttc tttatcatgc aactcgtagg acaggtgccg     1920
gcagcgctct gggtcatttt cggcgaggac cgctttcgct ggagcgcgac gatgatcggc     1980
ctgtcgcttg cggtattcgg aatcttgcac gccctcgctc aagccttcgt cactggtccc     2040
gccaccaaac gtttcggcga agcaggcc attatcgccg gcatggcggc cgacgcgctg     2100
ggctacgtct tgctggcgtt cgcgacgcga ggctggatgg ccttccccat tatgattctt     2160
ctcgcttccg gcggcatcgg gatgcccgcg ttgcaggcca tgctgtccag gcaggtagat     2220
gacgaccatc agggacagct tcaaggatcg ctcgcggctc ttaccagcct aacttcgatc     2280
actggaccgc tgatcgtcac ggcgatttat gccgcctcgg cgagcacatg gaacgggttg     2340
gcatggattg taggcgccgc cctataccctt gtctgcctcc ccgcgttgcg tcgcggtgca     2400
tggagccggg ccacctcgac ctgaatggaa gccggcggca cctcgctaac ggattcacca     2460
```

```
ctccaagaat tggagccaat caattcttgc ggagaactgt gaatgcgcaa accaaccctt    2520
ggcagaacat atccatcgcg tccgccatct ccagcagccg cacgcggcgc atctcgggca    2580
gcgttgggtc ctggccacgg gtgcgcatga tcgtgctcct gtcgttgagg acccggctag    2640
gctggcgggg ttgccttact ggttagcaga atgaatcacc gatacgcgag cgaacgtgaa    2700
gcgactgctg ctgcaaaacg tctgcgacct gagcaacaac atgaatggtc ttcggtttcc    2760
gtgtttcgta aagtctggaa acgcggaagt cccctacgtg ctgctgaagt tgcccgcaac    2820
agagagtgga accaaccggt gataccacga tactatgact gagagtcaac gccatgagcg    2880
gcctcatttc ttattctgag ttacaacagt ccgcaccgct gtccggtagc tccttccggt    2940
gggcgcgggg catgactatc gtcgccgcac ttatgactgt cttctttatc atgcaactcg    3000
taggacaggt gccggcagcg cccaacagtc ccccggccac ggggcctgcc accatcccca    3060
cgccgaaaca agcgccctgc accattatgt tccggatctg catcgcagga tgctgctggc    3120
taccctgtgg aacacctaca tctgtattaa cgaagcgcta accgttttta tcaggctctg    3180
ggaggcagaa taaatgatca tatcgtcaat tattacctcc acggggagag cctgagcaaa    3240
ctggcctcag gcatttgaga agcacacggt cacactgctt ccggtagtca ataaaccggt    3300
aaaccagcaa tagacataag cggctattta acgaccctgc cctgaaccga cgaccgggtc    3360
gaatttgctt tcgaatttct gccattcatc cgcttattat cacttattca ggcgtagcac    3420
caggcgttta agggcaccaa taactgcctt aaaaaaatta cgccccgccc tgccactcat    3480
cgcagtactg ttgtaattca ttaagcattc tgccgacatg gaagccatca cagacggcat    3540
gatgaacctg aatcgccagc ggcatcagca ccttgtcgcc ttgcgtataa tatttgccca    3600
tggtgaaaac gggggcgaag aagttgtcca tattggccac gtttaaatca aaactggtga    3660
aactcaccca gggattggct gagacgaaaa acatattctc aataaaccct ttagggaaat    3720
aggccaggtt ttcaccgtaa cacgccacat cttgcgaata tatgtgtaga aactgccgga    3780
aatcgtcgtg gtattcactc cagagcgatg aaaacgtttc agtttgctca tggaaaacgg    3840
tgtaacaagg gtgaacacta tcccatatca ccagctcacc gtctttcatt gccatacg     3898
```

RECOMBINANT MICROORGANISM FOR IMPROVED PRODUCTION OF FINE CHEMICALS

CROSS-REFERENCE TO RELATED APPLICATIONS

This application is a national stage application (under 35 U.S.C. § 371) of PCT/EP2016/055582, filed Mar. 15, 2016, which claims benefit of U.S. Application Nos. 62/134,607, 62/134,608, 62/134,610, and 62/134,611, all filed Mar. 18, 2015, all of which are incorporated herein by reference in their entirety.

FIELD OF THE INVENTION

The present invention relates to a recombinant microorganism, to a method for producing alanine and to the use of the recombinant microorganism for the fermentative production of alanine.

DESCRIPTION OF THE INVENTION

Amino acids are organic compounds with a carboxy-group and an amino-group. The most important amino acids are the alpha-amino acids where the amino group is located next to the carboxy-group. Proteins are based on alpha-amino acids.

Alanine has drawn considerable interest because it has been used as an additive in the food, feed and pharmaceutical industries. Moreover alanine is a raw material for the industrial production of alanine, N,N-bis(carboxymethyl)-, trisodium salt (MGDA, trade name TRILON® M, BASF SE, Ludwigshafen, Germany) which is a strong chelating agent, showing an excellent performance at dissolving organic and inorganic scale (WO94/29421, WO02012/150155). TRILON® M grades are readily biodegradable according to standard OECD tests. Due to the superb ecological and toxicological profile, TRILON® M grades are particularly suitable for use in products for end-consumers and the demand for such biodegradable complex builders is constantly rising.

Alanine can be produced by fermentation with Coryneform bacteria (Hermann, 2003: Industrial production of amino acids by Coryneform bacteria, J. of Biotechnol, 104, 155-172.) or E. coli. (WO2007/120198, WO2008/119009).

Alanine production in E. coli is more efficient and widely used for industrial production of alanine as raw material for the chemical industry. As the demand of the chemical industry for alanine is increasing, there is a demand for improvement of productivity of fermentative production of alanine.

It is one object of the present invention to provide microorganisms which can be used in fermentative production of alanine with high yield and efficiency.

DETAILED DESCRIPTION OF THE INVENTION

A contribution to achieving the above mentioned aim is provided by a recombinant microorganism of the family of Escherichia coli (E. coli) having, compared to a respective reference microorganism, an introduced, increased or enhanced activity and/or expression of a gcvTHP operon.

The term "higher", "increase" or "enhanced" e.g. in reference to expression and/or activity of an enzyme or to yield or productivity, means a significantly higher, increased or enhanced expression and/or activity or yield or productivity.

The term "reduced, repressed or deleted expression and/or activity of an enzyme", means a significantly reduced, repressed or deleted expression and/or activity and also encompasses an undetectable expression and/or activity of the respective enzymes.

Surprisingly, it has been discovered that a microorganism having an introduced, increased or enhanced activity and/or expression of the proteins encoded by the gcvTHP operon has a higher yield and/or productivity of alanine in fermentative production when compared to the same microorganism not comprising an introduced, increased or enhanced activity and/or expression of the respective gcvTHP operon.

Accordingly, one embodiment of the invention at hand is a recombinant microorganism comprising compared to a respective reference microorganism an introduced, increased or enhanced activity and/or expression of a gcvTHP operon encoding each of a gcvH gene, encoding a lipoylprotein of the glycine cleavage complex, a gcvP gene encoding a pyridoxal phosphate-dependent glycine decarboxylase and a gcvT gene encoding a tetrahydrofolate-dependent aminomethyltransferase and having compared to a respective reference microorganism a higher yield and/or productivity of alanine in fermentative production.

The term "reference microorganism" as used herein means a control microorganism to which the recombinant microorganism is compared. This reference microorganism has substantially the same genotype as the recombinant microorganism with the exception of the difference to be analyzed. Preferably the reference microorganism is the strain from which the recombinant microorganism is originated. For example, a gene has been introduced into a wild type microorganism, thus creating a recombinant microorganism, in this case the wild type would be a suitable reference microorganism for this recombinant microorganism. It is also possible, that into a recombinant microorganism A a further mutation is introduced, thereby creating a recombinant microorganism B. The recombinant microorganism A would then be the suitable reference microorganism for recombinant microorganism B. In the event, the performance of a recombinant microorganism and the respective reference microorganism shall be compared both microorganisms are grown under substantially identical conditions.

It is obvious for the skilled person that a microorganism having an increased yield and/or productivity of alanine can also be used for the production of other metabolites that are closely related to alanine, for example metabolites that are intermediates in the alanine pathway, that share common intermediates with the alanine pathway or that are metabolites which use alanine as intermediate in their pathway. The microorganisms of the invention can also be easily adapted for having an increased yield and/or productivity of such related metabolites by increasing or introducing certain enzyme activities or by knocking out or decreasing certain enzyme activities.

Such metabolites are for example pyruvate, succinate, aspartate, malate, lactate, valine and leucine.

For example, in order to use the recombinant microorganism of the invention to produce succinate, the genes ldh, pfl, pta and adhE have to be knocked out and a PEP carboxylase gene and/or a pyruvate carboxylase gene have to be introduced in the genome of the microorganism of the invention. The respective pathway and necessary mutations are described for example in Zhang et al. (2009), PNAS (106) pp 20180-20185.

Accordingly, another embodiment of the invention at hand is a recombinant microorganism comprising compared to a respective reference microorganism an introduced, increased or enhanced activity and/or expression of a gcvTHP operon and having compared to a respective reference microorganism a higher yield and/or productivity of pyruvate, succinate, aspartate, malate, lactate, valine and/or leucine in fermentative production.

In some embodiments, the microorganism is a prokaryotic cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp.* CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosterone, Pseudomonas aeruginosa, Rhodococcus erythropolis, Rhodococcus rhodochrous, Rhodococcus sp.* ATCC 15592, *Rhodococcus sp.* ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth.

In some embodiments, the microorganism is a eukaryotic cell. Suitable eukaryotic cells include yeast cells, as for example *Saccharomyces* spec, such as *Saccharomyces cerevisiae, Hansenula* spec, such as *Hansenula polymorphs, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia.*

Numerous bacterial industrial strains are especially suitable for use in the methods disclosed herein. In some embodiments, the microorganism is a species of the genus *Corynebacterium*, e.g. *C. acetophilum, C. glutamicum, C. callunae, C. acetoacidophilum, C. acetoglutamicum*. In some embodiments, the microorganism is a species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformic, B. clausii, B. stearothermophilus, B. halodurans, B. subtilis, B. pumilus,* and *B. amyloliquefaciens*. In some embodiments, the microorganism is a species of the genus *Erwinia*, e.g., *E. uredovora, E. carotovora, E. ananas, E. herbicola, E. punctata* and *E. terreus*. In some embodiments, the microorganism is a species of the genus *Escherichia*, e.g., *E. coli*. In other embodiments the microorganism is a species of the genus *Pantoea*, e.g., *P. citrea* or *P. agglomerans*. In still other embodiments, the microorganism is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*. In further embodiments, the microorganism is a species of the genus *Zymomonas*, e.g., *Z. mobilis* or *Z. lipolytica*. In further embodiments, the microorganism is a species of the genus *Rhodococcus*, e.g. *R. opacus.*

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

In addition to the introduced, increased or enhanced activity and/or expression of a gcvTHP operon, the recombinant microorganism of the invention may further comprise (a) a reduced, repressed or deleted activity and/or expression of a pflB gene encoding a pyruvate formate lyase I, wherein the reduction, repression or deletion of the activity and/or expression of the pflB gene is determined compared to a respective reference microorganism.

In addition to the introduced, increased or enhanced activity and/or expression of a gcvTHP operon, the recombinant microorganism of the invention may further comprise (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase), wherein the reduction, repression or deletion of the activity and/or expression of the adhE gene is determined compared to a respective reference microorganism.

In addition to the introduced, increased or enhanced activity and/or expression of a gcvTHP operon, the recombinant microorganism of the invention may further comprise (c) a reduced, repressed or deleted activity and/or expression of a ldhA gene encoding a NAD-dependent fermentative D-lactate dehydrogenase, wherein the reduction, repression or deletion of the activity and/or expression of the ldhA gene is determined compared to a respective reference microorganism.

In addition to the introduced, increased or enhanced activity and/or expression of a gcvTHP operon, the recombinant microorganism of the invention may further comprise (d) a reduced, repressed or deleted activity and/or expression of a pta gene encoding a phosphate acetyltransferase, wherein the reduction, repression or deletion of the activity and/or expression of the pta gene is determined compared to a respective reference microorganism.

In addition to the introduced, increased or enhanced activity and/or expression of a gcvTHP operon, the recombinant microorganism of the invention may further comprise (e) a reduced, repressed or deleted activity and/or expression of a frdA gene encoding a fumarate reductase, wherein the reduction, repression or deletion of the activity and/or expression of the frdA gene is determined compared to a respective reference microorganism.

In addition to the introduced, increased or enhanced activity and/or expression of a gcvTHP operon, the recombinant microorganism of the invention may further comprise (f) an introduced, increased or enhanced activity and/or expression of an alaD gene encoding an alanine dehydrogenase, wherein the increase or enhancement of the activity and/or expression of the alaD gene is determined compared to a respective reference microorganism.

Preferably, the recombinant microorganism of the invention comprising the introduced, increased or enhanced activity and/or expression of a gcvTHP operon is additionally having at least two, more preferably at least three, even more preferably at least four, even more preferably at least five, most preferably all of the features selected from the group of
(a) a reduced, repressed or deleted activity and/or expression of a pflB gene encoding a pyruvate formate lyase I and
(b) a reduced, repressed or deleted activity and/or expression of a adhE gene encoding a bifunctional acetaldehyde-CoA dehydrogenase/iron-dependent alcohol dehydrogenase/pyruvate-formate lyase deactivase) and
(c) a reduced, repressed or deleted activity and/or expression of a ldhA gene encoding a NAD-dependent fermentative D-lactate dehydrogenase and
(d) a reduced, repressed or deleted activity and/or expression of a pta gene encoding a phosphate acetyltransferase and
(e) a reduced, repressed or deleted activity and/or expression of a frdA gene encoding a fumarate reductase and
(f) an introduced, increased or enhanced activity and/or expression of an alaD gene encoding an alanine dehydrogenase,
wherein the reduction, repression, deletion, increase or enhancement of the activity and/or expression of a gene is determined compared to a respective reference microorganism.

The alaD gene may be derived from any organism or may be a synthetic gene designed by man, for example having codon usage optimized for expression in the recombinant microorganism of the invention or being optimized for enzyme activity, e.g. having improved Vmax or Km. Preferably the alaD gene is derived from a microorganism of one of the geni *Bacillus, Geobacillus, Paenibacillus, Halobacillus, Brevibacillus*. In a more preferred embodiment the alaD gene is derived from a microorganism of the genus *Geobacillus*. In a most preferred embodiment, the alaD gene is derived from *Geobacillus stearothermophilus*.

In a preferred embodiment the alaD gene has been codon optimized for the expression in the recombinant microorganism of the invention.

The microorganism of the invention may comprise further genetic modifications, such as mutations, knock-outs or enhanced or introduced enzyme activities that further improve yield and/or productivity of alanine, pyruvate, succinate, aspartate, malate, lactate, valine and/or leucine, preferably succinate or alanine, more preferably alanine. For example, the microorganism of the invention may further comprise an enhanced or increased expression and/or activity of the ygaW gene from *E. coli* or homologs or functional equivalents thereof which has recently been described to improve alanine productivity of a microorganism when overexpressed (WO2012/172822).

In another example, the microorganism of the invention may in addition comprise an introduced, increased or enhanced activity and/or expression of an lpd gene encoding a lipoamide dehydrogenase protein.

In a further example, the microorganism of the invention may in addition comprise any one of, any combination of or all of the genes that are specified and described in detail in the applications PCT/IB2014/064426 and PCT/IB2014/066686 and that are beneficial for production of alanine, pyruvate, succinate, aspartate, malate, lactate, valine and/or leucine, preferably succinate or alanine, more preferably alanine.

In a further embodiment the gcvTHP operon encoding each of a gcvH gene, encoding a lipoylprotein of the glycine cleavage complex, a gcvP gene encoding a pyridoxal phosphate-dependent glycine decarboxylase and a gcvT gene encoding a tetrahydrofolate-dependent aminomethyltransferase with an introduced, increased or enhanced activity and/or expression in the recombinant microorganism of the invention, is selected from the group of
(i) a nucleic acid molecule comprising a sequence of SEQ ID NO: 51, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 51, or
(iii) a nucleic acid molecule hybridizing to a nucleic acid molecule having SEQ ID NO: 51 under medium stringent conditions, more preferably under high stringent conditions, most preferably under very high stringent conditions, or
(iv) a nucleic acid molecule encoding each of the polypeptides of SEQ ID NO: 46, 48 and 50 or
(v) a nucleic acid molecule encoding each of a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 46, and a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 48 and a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 50,
wherein the polypeptides encoded by (ii), (iii) or (v) are having at least 10%, 20% preferably at least 30% or 50%, more preferably at least 60% or 70%, even more preferably at least 75%, 80%, 85% or 90%, most preferred at least 95% of the activity as the polypeptides having SEQ ID NO: 46, 48 or 50 respectively.

The recombinant microorganism of the invention comprising the introduced, increased or enhanced expression and/or activity of the gcvTHP operon may further comprise an lpd gene which may for example have the sequence of SEQ ID NO: 1 or 3, a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1 or 3, or a nucleic acid molecule hybridizing to a nucleic acid molecule of SEQ ID NO: 1 or 3 under medium stringent conditions, more preferably under high stringent conditions, most preferably under very high stringent conditions, each of the nucleic acids encoding a polypeptide of SEQ ID NO: 2 or 4 or encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 2 or 4, wherein the polypeptide is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 2 or 4.

The recombinant microorganism of the invention comprising the introduced, increased or enhanced expression and/or activity of the gcvTHP operon may further comprise any one, two, three, four, five or all of the features as defined above under (a) to (f), wherein the pflB gene is selected from the group consisting of (A) a nucleic acid molecule comprising a sequence of SEQ ID NO: 5, or
(B) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 5, or
(C) a nucleic acid molecule hybridizing to a nucleic acid molecule having SEQ ID NO: 5 under medium stringent conditions, more preferably under high stringent conditions, most preferably under very high stringent conditions, or
(D) a nucleic acid molecule encoding a polypeptide of SEQ ID NO: 6, or
(E) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 6, wherein the polypeptide encoded by (B), (C) or (E) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 6 and wherein the adhE gene is selected from the group consisting of (F) a nucleic acid molecule comprising a sequence of SEQ ID NO: 7, or
(G) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 7, or
(H) a nucleic acid molecule hybridizing to a nucleic acid molecule having SEQ ID NO: 7 under medium stringent conditions, more preferably under high stringent conditions, most preferably under very high stringent conditions, or
(I) a nucleic acid molecule encoding a polypeptide of SEQ ID NO: 8, or
(J) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 8, wherein the polypeptide encoded by (G), (H) or (J) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 8 and wherein the ldhA gene is selected from the group consisting of (K) a nucleic acid molecule comprising a sequence of SEQ ID NO: 9, or
(L) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 9, or
(M) a nucleic acid molecule hybridizing to a nucleic acid molecule having SEQ ID NO: 9 under medium stringent conditions, more preferably under high stringent conditions, most preferably under very high stringent conditions, or
(N) a nucleic acid molecule encoding a polypeptide of SEQ ID NO: 10, or
(O) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 10, wherein the polypeptide encoded by (L), (M) or (O) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 10 and wherein the pta gene is selected from the group consisting of (P) a nucleic acid molecule comprising a sequence of SEQ ID NO: 11, or
(Q) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 11, or
(R) a nucleic acid molecule hybridizing to a nucleic acid molecule having SEQ ID NO: 11 under medium stringent conditions, more preferably under high stringent conditions, most preferably under very high stringent conditions, or (S) a nucleic acid molecule encoding a polypeptide of SEQ ID NO: 12, or (T) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 12, wherein the polypeptide encoded by (Q), (R) or (T) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 12 and wherein the frdA gene is selected from the group consisting of (U) a nucleic acid molecule comprising a sequence of SEQ ID NO: 13, or (V) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 13, or (W) a nucleic acid molecule hybridizing to a nucleic acid molecule having SEQ ID NO: 13 under medium stringent conditions, more preferably under high stringent conditions, most preferably under very high stringent conditions, or (X) a nucleic acid molecule encoding a polypeptide of SEQ ID NO: 14, or (Y) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 14, wherein the polypeptide encoded by (V), (W) or (Y) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 14 and wherein the alaD gene is selected from the group consisting of (Z) a nucleic acid molecule comprising a sequence of SEQ ID NO: 15, or (AA) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 15, or (BB) a nucleic acid molecule hybridizing to a nucleic acid molecule having SEQ ID NO: 15 under medium stringent conditions, more preferably under high stringent conditions, most preferably under very high stringent conditions, or (CC) a nucleic acid molecule encoding a polypeptide of SEQ ID NO: 16, or (DD) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEC) ID NO: 16, wherein the polypeptide encoded by (AA), (BB) or (DD) is having at least 10%, 20% preferably at least 30% or 50%, more preferably at least 60% or 70%, even more preferably at least 75%, 80%, 85% or 90%, most preferred at least 95% of the activity as the polypeptide having SEC) ID NO: 16.

A further embodiment of the invention is a composition comprising one or more recombinant microorganisms of the invention as defined above. The composition may further comprise a medium that allows growth of the recombinant microorganism of the invention. The medium may additionally comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose of sucrose, more preferably the carbon source is glucose.

In a preferred embodiment the composition comprises the microorganism of the invention and NBS medium, AM1 medium or PPM01 medium. More preferably the composition further comprises a carbon source, preferably a sugar. The ingredients of these media are known to a skilled person.

Preferably NBS medium comprises per liter
1-5 g, preferably 3.5 g $KH_2PO_4$ and
1-10 g, preferably 5.0 g $K_2HPO_4$ and
1-5 g, preferably 3.5 g $(NH_4)_2HPO_4$ and
0.1-1 g, preferably 0.25 g $MgSO_4\text{-}7H_2O$ and
5-25 mg, preferably 15 mg $CaCL_2\text{-}2H_2O$ and
0.1-1 mg, preferably 0.5 mg Thiamine and
0.1-5 ml, preferably 1 ml trace metal stock,
wherein the trace metal stock comprises 0.5-5 g, preferably 1.6 g $FeCL_3\text{-}6H_2O$; 0.05-0.5 g, preferably 0.2 g $CoCl_2\text{-}6H_2O$; 0.01-0.5 g, preferably 0.1 g $CuCl_2\text{-}2H_2O$; 0.1-0.5 g, preferably 0.2 g $ZnCl_2$; 0.05-0.5 g, preferably 0.2 g $NaMoO_4\text{-}2H_2O$; 0.001-0.1 g, preferably 0.05 g $H_3BO_3$ per liter 0.01-1 M, preferably 0.1 M HCL.

The preferred carbon source in the NBS medium is glucose or sucrose, preferably 2%-18% glucose or 2%-16% sucrose.

Preferably AM 1 medium comprises per liter 0.1-10 mM, preferably 1 mM betain solution
1-10 g, preferably 2.6 g $(NH_4)_2HPO_4$ and
0.1-5 g, preferably 0.87 g $NH_4H_2PO_4$ and
0.05-2.5 g, preferably 0.15 g KCl and
0.05-5 g, preferably 0.37 g $MgSO_4\text{-}7H_2O$ and
0.1-5 ml, preferably 1 ml trace metal stock,
wherein the trace metal stock comprises per liter 0.01-1 M, preferably 0.12 M HCL, 1-5 g, preferably 2.4 g $FeCL_3\text{-}6H_2O$; 0.1-1 g, preferably 0.3 g $CoCl_2\text{-}6H_2O$; 0.1-1 g, preferably 0.21 g $CuCl_2\text{-}2H_2O$; 0.1-1 g, preferably 0.3 g $ZnCl_2$; 0.1-1 g, preferably 0.27 g $NaMoO_4\text{-}2H_2O$; 0.01-0.5 g, preferably 0.068 g $H_3BO_3$ and 0.1-1 g, preferably 0.5 g $MnCl_2\text{-}4H_2O$, and optionally 1-30 g, preferably 15 g $(NH_4)_2SO_4$.

The preferred carbon source in the AM 1 medium is glucose or sucrose, preferably 2%-18% glucose or 2%-16% sucrose.

Preferably PPM01 medium comprises per liter
0.05-5 g, preferably 0.37 g $MgSO_4\text{-}7H_2O$ and
0.1-10 g, preferably 1 g $(NH_4)_2SO_4$ and
0.05-5 g, preferably 0.46 g betaine and
0.001-0.5 g, preferably 0.05 g Cyanocobalamin (B12) and
1-10 g, preferably 3.74 g $KH_2PO_4$ and
0.1-5 ml, preferably 1 ml trace metal stock,
wherein the trace metal stock comprises per liter 10-100 mM, preferably 60 mM sulfuric acid, 1-10 g, preferably 3.48 g $(NH_4)_2Fe(II)(SO_4)_2 \cdot 7H_2O$; 0.1-1 g, preferably 0.35 g $CoSO_4 \cdot 7H_2O$; 0.1-1 g, preferably 0.31 g $CuSO_4 \cdot 5H_2O$; 0.1-5 g, preferably 0.63 g $ZnSO_4 \cdot 7H_2O$; 0.1-1 g, preferably 0.27 g $MnSO_4$—$H_2O$; 0.01-1 g, preferably 0.07 g $NaMoO_4 \cdot 2H_2O$ and 0.1-5 g, preferably 0.43 g $H_3BO_3$.

The preferred carbon source in the PPM01 medium is glucose monohydrate, preferably 10-500 g, more preferably 140 g glucose monohydrate per liter medium.

A further embodiment of the invention is a method for producing a recombinant microorganism with enhanced alanine, pyruvate, succinate, aspartate, malate, lactate, valine and/or leucine, preferably succinate or alanine, more preferably alanine yield or productivity, which comprises the following steps:
(I) introducing, increasing or enhancing of one or more activity and/or expression of the gcvTHP operon or as defined above under (i) to (v) in a microorganism; and
(II) generating, identifying and isolating a recombinant microorganism with enhanced alanine, pyruvate, succinate, aspartate, malate, lactate, valine and/or leucine, preferably succinate or alanine, more preferably alanine yield or productivity compared to a corresponding microorganism without introduced, increased or enhanced activity and/or expression of the gcvTHP operon or as defined above under (i) to (v).

In a preferred embodiment of the method for producing a recombinant microorganism of the invention the method further comprises the step of reducing, repressing or deleting the activity and/or expression of at least one, at least two, at least three, at least four or all of the pflB gene, adhE gene, ldhA gene, pta gene or frdA gene for example as defined above under (A) to (Y) and/or the step of introducing, increasing or enhancing activity and/or expression of an alaD gene for example as defined above under (Z) to (DD).

A more preferred method for producing a recombinant microorganism of the invention comprises the step of reducing, repressing or deleting the activity and/or expression of all of the pflB gene, adhE gene, ldhA gene, pta gene and frdA gene and the step of introducing, increasing or enhancing activity and/or expression of an alaD gene and a gcvTHP operon.

The method for producing a recombinant microorganism of the invention may further comprise the step of introducing, increasing or enhancing activity and/or expression of an lpd gene.

Moreover the method for producing a recombinant microorganism of the invention may further comprise the step of reducing, repressing or deleting additional genes that are specified and described in detail in the applications PCT/IB2014/064426 and PCT/IB2014/066686 and the reduction, repression or deletion of which is beneficial for production of alanine, pyruvate, succinate, aspartate, malate, lactate, valine and/or leucine, preferably succinate or alanine, more preferably alanine, most preferably L-alanine.

Moreover the method for producing a recombinant microorganism of the invention may further comprise the step of introducing, increasing or enhancing activity and/or expression of additional genes that are specified and described in detail in the applications PCT/IB2014/064426 and PCT/IB2014/066686 and the introduction, increases or enhancement of the activity and/or expression of which is beneficial for production of alanine, pyruvate, succinate, aspartate, malate, lactate, valine and/or leucine, preferably succinate or alanine, more preferably alanine, most preferably L-alanine.

In one embodiment of the method for producing a recombinant microorganism of the invention the microorganism is selected from the group consisting of species of the genus *Corynebacterium*, e.g. *C. acetophilum*, *C. glutamicum*, *C. callunae*, *C. acetoacidophilum*, *C. acetoglutamicum*, species of the genus *Bacillus*, e.g., *B. thuringiensis*, *B. anthracia*, *B. megaterium*, *B. subtilis*, *B. lentils*, *B. circulans*, *B. pumilus*, *B. lautus*, *B. coagulans*, *B. brevis*, *B. firmus*, *B. alkaophius*, *B. licheniformis*, *B. clausii*, *B. stearothermophilus*, *B. halodurans*, *B. subtilis*, *B. pumilus*, and *B. amyloliquefaciens*, species of the genus *Erwinia*, e.g., *E. uredovora*, *E. carotovora*, *E. ananas*, *E. herbicola*, *E. punctate*, *E. terreus*, species of the genus *Escherichia*, e.g., *E. coli*, species of the genus *Pantoea*, e.g., *P. citrea*, *P. agglomerans*, species of the genus *Streptomyces*, e.g., *S. ambofaciens*, *S. achromogenes*, *S. avermitilis*, *S. coelicolor*, *S. aureofaciens*, *S. aureus*, *S. fungicidicus*, *S. griseus*, *S. lividans*, species of the genus *Zymomonas*, e.g., *Z. mobilis* or *Z. lipolytica* and species of the genus *Rhodococcus*, e.g. *R. opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

A further embodiment of the invention is a method of producing alanine, pyruvate, succinate, aspartate, malate, lactate, valine and/or leucine, preferably succinate or alanine, more preferably alanine, most preferably L-alanine, comprising culturing one or more recombinant microorganism as defined above under conditions that allow for the production of alanine, pyruvate, succinate, aspartate, malate, lactate, valine and/or leucine, preferably succinate or alanine, more preferably alanine, most preferably L-alanine.

In some embodiments, the recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 34° C., 35° C. or 36° C. In a most preferred embodiment the temperature is about 37° C. or 38° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 7.

In one embodiment of the method of producing alanine, pyruvate, succinate, aspartate, malate, lactate, valine and/or leucine, preferably succinate or alanine, more preferably alanine, the microorganism is cultured in a medium comprising between 1% and 30% (w/v) of a sugar, between 5% and 25% (w/v) of a sugar, between 10% and 20% (w/v) of a sugar, between 12% and 18% (w/v) of a sugar. Preferably the microorganism is cultured in a medium comprising between 12% and 16% (w/v) of a sugar.

In another embodiment of the method for producing alanine, pyruvate, succinate, aspartate, malate, lactate, valine and/or leucine, preferably succinate or alanine, more preferably alanine the yield of alanine, pyruvate, succinate, aspartate, malate, lactate, valine and/or leucine is at least 80% for example at least 81%, at least 82%, at least 83%, at least 84% or at least 85%. Preferably the yield is at least 86%, at least 87%, at least 88%, at least 89% or at least 90%. More preferably the yield is at least 90.5%, at least 91%, at least 91.5%, at least 92%, at least 92.5%, at least 93%, at least 93.5%, at least 94% or at least 94.5%. In an even more preferred embodiment the yield is at least 95% or at least 95.5%. In a most preferred embodiment, the yield is at least 96%. The percent yield is calculated as gram product produced from gram glucose in the medium. Hence, when the medium contained 100 g glucose and the fermentation yielded 98 g alanine, the yield would be 98%.

In another embodiment of the method for producing alanine preferably L-alanine is produced, wherein the chiral purity of L-alanine is at least 90%, at least 91%, at least 92%, at least 93% or at least 94%. In a preferred embodiment the chiral purity of L-alanine is at least 95% or at least 95.5%. In a more preferred embodiment, the chiral purity of L-alanine is at least 96% or at least 96.5% or at least 97%. In an even more preferred embodiment the chiral purity of L-alanine is at least 97.5%, at least 98% or at least 98.5% for example at least 99%. Even more preferably the chiral purity of L-alanine is at least 99.5% or at least 99.6% for example at least 99.7%, at least 99.8%, or at least 99.9%. In a most preferred embodiment chiral pure L-alanine is produced.

Another embodiment of the invention is a method of culturing or growing any of the genetically modified microorganisms as defined above, the method comprising inoculating a culture medium with one or more genetically modified microorganism and culturing or growing said genetically modified microorganism in culture medium under conditions as defined above.

The use of a recombinant microorganism as defined above or a composition as defined above for the fermentative production of alanine, pyruvate, succinate, aspartate, malate, lactate, valine and/or leucine, preferably succinate or alanine, more preferably alanine, most preferably L-alanine is an additional embodiment of the invention.

The recombinant microorganism according to the present invention is characterized in that, compared to a respective reference microorganism for example a wild type, the expression and/or the activity of the enzymes that are encoded by the gcvTHP operon are increased.

In one embodiment the decrease of the expression and/or activity of a gene is achieved by a deactivation, mutation or knock-out of the gene. This could be done by deletion of part or total of the coding region and/or the promoter of the gene, by mutation of the gene such as insertion or deletion of a number of nucleotides for example one or two nucleotides leading to a frameshift in the coding region of the gene, introduction of stop codons in the coding region, inactivation of the promoter of the gene by for example deleting or mutating promoter boxes such as ribosomal entry sides, the TATA box and the like. The decrease may also be achieved by degrading the transcript of the gene for example by means of introduction of ribozymes, dsRNA, antisense RNA or antisense oligonucleotides. The decrease of the activity of a gene may be achieved by expressing antibodies or aptamers in the cell specifically binding the target enzyme. Other methods for the decrease of the expression and/or activity of a gene are known to a skilled person.

The reduced expression and/or activity of the enzymes disclosed herein, in particular the reduced expression and/or reduced activity of the enzyme encoded by the lactate dehydrogenase (ldhA), pyruvate formate lyase I (pflB), bifunctional acetaldehyde-CoA dehydrogenase/iron-dependent alcohol dehydrogenase/pyruvate-formate lyase deactivase (adhE), phosphate acetyltransferase (pta) and/or fumarate reductase (frdA), can be a reduction of the expression and/or enzymatic activity by at least 50%, compared to the expression and/or activity of said enzyme in a respective reference microorganism for example the wild type of the microorganism, or a reduction of the expression and/or enzymatic activity by at least 90%, or more preferably a reduction of expression and/or the enzymatic activity by at least 95%, or more preferably an expression and/or reduction of the enzymatic activity by at least 98%, or even more preferably a reduction of the expression and/or enzymatic activity by at least 99% or even more preferably a reduction of the expression and/or the enzymatic activity by at least 99.9%. In a most preferred embodiment the expression and/or activity of the enzymes is not detectable in the microorganism of the invention.

The enhanced or increased expression and/or activity of the enzymes disclosed herein, in particular the enhanced or increased expression and/or activity of the enzymes encoded by the gcvTHP operon, can be an increase of the expression and/or enzymatic activity by at least 25%, compared to the expression and/or activity of said enzyme in a respective reference microorganism for example the wild type of the microorganism, or an increase of the expression and/or enzymatic activity by at least 50%, or more preferably an increase of expression and/or the enzymatic activity by at least 100%, or more preferably an increase of the expression and/or of the enzymatic activity by at least 3 fold, for example at least 5 fold, or even more preferably an increase of the expression and/or enzymatic activity by at least 10 fold or even more preferably an increase of the expression and/or the enzymatic activity by at least 20 fold.

The increase of the expression and/or activity of the gcvTHP operon leads to an improved yield and/or productivity of alanine, pyruvate, succinate, aspartate, malate, lactate, valine and/or leucine, preferably succinate or alanine, more preferably alanine in the recombinant microorganism of the invention compared to a respective reference microorganism. Therefore the increase of the expression and/or activity of the gcvTHP operon may be determined by measuring alanine, pyruvate, succinate, aspartate, malate, lactate, valine and/or leucine, preferably succinate or alanine, more preferably alanine yield or productivity of the recombinant microorganism of the invention compared to a respective reference microorganism. Methods for fermentative production of metabolites, for example alanine are known to a skilled person and also described herein. Improved yield of e.g. alanine in fermentation by the microorganism of the invention compared to yield of alanine in fermentation by a respective reference microorganism is a measure for the increase of expression and or activity of the gcvTHP operon.

Methods for determining the lactate dehydrogenase (ldhA) expression or activity are, for example, disclosed by Bunch et al. in "The ldhA gene encoding the fermentative lactate dehydrogenase of *Escherichia coli*", Microbiology (1997), Vol. 143, pages 187-155; or Bergmeyer, H. U., Bergmeyer J. and Grassi, M. (1983-1986) in "Methods of Enzymatic Analysis", 3rd Edition, Volume III, pages 126-133, Verlag Chemie, Weinheim; or Enzymes in Industry; Production and Applications, Second Edition (2004), Wolfgang Aehle, page 23. Preferred is the last method.

Methods for determining the pyruvate formate lyase I (pflB) expression or activity are, for example, disclosed in Knappe J, Blaschkowski H P, Grobner P, Schmitt T (1974). "Pyruvate formate-lyase of *Escherichia coli*: the acetyl-enzyme intermediate." Eur J Biochem 1974; 50(1); 253-63. PMID: 4615902; in KNAPPE, Joachim, et al. "Pyruvate Formate-Lyase of *Escherichia coli*: the Acetyl-Enzyme Intermediate." European Journal of Biochemistry 50.1 (1974): 253-263; in Wong, Kenny K., et al. "Molecular properties of pyruvate formate-lyase activating enzyme." Biochemistry 32.51 (1993): 14102-14110 and in Nnyepi, Mbako R., Yi Peng, and Joan B. Broderick. "Inactivation of *E. coli* pyruvate formate-lyase: Role of AdhE and small molecules." Archives of biochemistry and biophysics 459.1 (2007): 1-9.

Methods for determining the bifunctional acetaldehyde-CoA dehydrogenase/iron-dependent alcohol dehydrogenase/pyruvate-formate lyase deactivase (adhE) expression or activity are, for example, disclosed in Membrillo-Hernandez, Jorge, et al. "Evolution of the adhE Gene Product of *Escherichia coli* from a Functional Reductase to a Dehydrogenase GENETIC AND BIOCHEMICAL STUDIES OF THE MUTANT PROTEINS." Journal of Biological Chemistry 275.43 (2000): 33869-33875 and in Mbako R. Nnyepi, Yi Peng, Joan B. Broderick, Inactivation of *E. coli* pyruvate formate-lyase: Role of AdhE and small molecules, Archives of Biochemistry and Biophysics, Volume 459, Issue 1, 1 Mar. 2007, Pages 1-9.

Methods for determining the phosphate acetyltransferase (pta) expression or activity are, for example, disclosed in Dittrich, Cheryl R., George N. Bennett, and Ka-Yiu San. "Characterization of the Acetate-Producing Pathways in *Escherichia coli*." Biotechnology progress 21.4 (2005): 1062-1067 and in Brown, T. D. K., M. C. Jones-Mortimer, and H. L. Kornberg. "The enzymic interconversion of acetate and acetyl-coenzyme A in *Escherichia coli*." Journal of general microbiology 102.2 (1977): 327-336, Methods for determining the fumarate reductase (frdA) expression or activity are, for example, disclosed in Dickie, Peter, and Joel H. Weiner. "Purification and characterization of membrane-bound fumarate reductase from anaerobically grown *Escherichia coli*." Canadian journal of biochemistry 57.6 (1979): 813-821; in Cecchini, Gary, et al. "Reconstitution of quinone reduction and characterization of *Escherichia coli* fumarate reductase activity." Journal of Biological Chemistry 261.4 (1986): 1808-1814 or in Schröder, I., et al. "Identification of active site residues of *Escherichia coli* fumarate reductase by site-directed mutagenesis." Journal of Biological Chemistry 266.21 (1991): 13572-13579.

Methods for determining the alanine dehydrogenase (alaD) expression or activity are, for example, disclosed in Sakamoto, Y., Nagata, S., Esaki, N., Tanaka, H., Soda, K. "Gene cloning, purification and characterization of thermostable alanine dehydrogenase of *Bacillus stearothermophilus*" J Fermen. Bioeng. 69 (1990):154-158.

The term "reduced expression of an enzyme" includes, for example, the expression of the enzyme by said genetically manipulated (e.g., genetically engineered) microorganism at a lower level than that expressed by a respective reference microorganism for example the wild type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more deleterious gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

A deleterious mutation according to this application is any mutation within a gene comprising promoter and coding region that lead to a decreased or deleted protein activity of the protein encoded by the coding region of the gene. Such deleterious mutations comprise for example frameshifts, introduction of stop-codons in the coding region, mutation of promoter elements such as the TATA box that prevent transcription and the like.

Microorganisms having an increased or enhanced expression and/or activity of the enzymes encoded by the gcvTHP operon may occur naturally, i.e. due to spontaneous mutations. A microorganism can be modified to have significantly increased activity of the enzyme that is encoded by one or more of said genes by various techniques, such as chemical treatment or radiation. To this end, microorganisms will be treated by, e.g., a mutagenizing chemical agent, X-rays, or UV light. In a subsequent step, those microorganisms which have an increased expression and/or activity of the enzyme that is encoded by one or more of said genes will be selected. Recombinant microorganisms are also obtainable by homologous recombination techniques which aim to substitute one or more of said genes with a corresponding gene that encodes for an enzyme which, compared to the enzyme encoded by the wild type gene, has an increased expression and/or activity.

According to one embodiment of the recombinant microorganism according to the present invention, an increase of the expression and/or activity of the enzymes encoded by the gcvTHP operon may be achieved by a modification of the gcvTHP operon, wherein this/these gene modification(s) is(are) preferably realized by multiplication of the copy-number of the gcvTHP operon in the genome of the microorganism, by introducing the genes on a self-replicating expression vector into the microorganism, by exchanging the promoter of the gcvTHP operon against a stronger promoter or by converting the endogenous promoter of the genes into a stronger promoter, e.g. by introducing point-mutations into the promoter sequence.

Further the activity of the gcvTHP operon may be enhanced by mutating the genes in order to achieve amino acid exchanges in the proteins which improve activity of the genes. Such methods are known to a skilled person.

Another embodiment of the invention at hand is a recombinant microorganism comprising compared to a respective reference microorganism an introduced, increased or enhanced activity and/or expression of a gcvT gene encoding a tetrahydrofolate-dependent aminomethyltransferase and having compared to a respective reference microorganism a higher yield and/or productivity of alanine in fermentative production.

Another embodiment of the invention at hand is a recombinant microorganism comprising compared to a respective reference microorganism an introduced, increased or enhanced activity and/or expression of a gcvH gene encoding a lipoylprotein of the glycine cleavage complex and having compared to a respective reference microorganism a higher yield and/or productivity of alanine in fermentative production.

Another embodiment of the invention at hand is a recombinant microorganism comprising compared to a respective reference microorganism an introduced, increased or enhanced activity and/or expression of a gcvP gene encoding a pyridoxal phosphate-dependent glycine decarboxylase and having compared to a respective reference microorganism a higher yield and/or productivity of alanine in fermentative production.

Furthermore another embodiment of the invention at hand is a recombinant microorganism comprising compared to a respective reference microorganism an introduced, increased or enhanced activity and/or expression of a gcvT gene and a gcvH gene or a gcvT gene and a gcvP gene or a gcvH and a gcvP gene and having compared to a respective reference microorganism a higher yield and/or productivity of alanine in fermentative production.

Furthermore another embodiment of the invention at hand is a recombinant microorganism comprising compared to a respective reference microorganism an introduced, increased or enhanced activity and/or expression of a gcvTHP operon in which the order of the open reading frames gcvT (SEQ ID NO: 45), gcvH (SEQ ID NO: 47), gcvP (SEQ ID NO: 49) is changed (resulting in an gcvPHT or gcvHPT or gcvTPH or gcvPTH or gcvHTP operon) having compared to a respective reference microorganism a higher yield and/or productivity of alanine in fermentative production.

A mutation into the above-gene(s) can be introduced, for example, by site-directed or random mutagenesis, followed by an introduction of the modified gene into the genome of the microorganism by recombination. Variants of the genes can be generated by mutating the gene sequences by means of PCR. The "Quickchange Site-directed Mutagenesis Kit" (Stratagene) can be used to carry out a directed mutagenesis.

A random mutagenesis over the entire coding sequence, or else only part thereof, can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

In the following, a suitable technique for recombination, in particular for introducing a mutation or for deleting sequences, is described.

This technique is also sometimes referred to as the "Campbell recombination" herein (Leenhouts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

In one embodiment the induction of the expression and/or activity of the enzymes encoded by the gcvTHP operon is achieved by an activation of the gcvTHP operon.

The terms "alanine, pyruvate, succinate, aspartate, malate, lactate, valine and/or leucine", as used in the context of the present invention, has to be understood in their broadest sense and also encompasses salts thereof, as for example alkali metal salts, like $Na^+$ and $K^+$-salts, or earth alkali salts, like $Mg^{2+}$ and $Ca^{2+}$-salts, or ammonium salts or anhydrides of alanine, pyruvate, succinate, aspartate, malate, lactate, valine and/or leucine.

Preferably, alanine, pyruvate, succinate, aspartate, malate, lactate, valine and/or leucine, preferably succinate or alanine, more preferably alanine is produced under microaerobic conditions. Aerobic or anaerobic conditions may be also used.

Microaerobic means that the concentration of oxygen is less than that in air. According to one embodiment microaerobic means oxygen tension between 5 and 27 mm Hg, preferably between 10 and 20 Hg (Megan Falsetta et al. (2011), The composition and metabolic phenotype of Neisseria gonorrhoeae biofilms, Frontiers in Microbiology, Vol 2, page 1 to 11). Preferably the microaerobic conditions are established with 0.1 to 1 vvm air flow.

Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

According to one embodiment of the process according to the present invention the assimilable carbon source may be glucose, glycerin, glucose, maltose, maltodextrin, fructose, galactose, mannose, xylose, sucrose, arabinose, lactose, raffinose and combinations thereof.

In a preferred embodiment the assimilable carbon source is glucose, sucrose, xylose, arabinose, glycerol or combinations thereof. Preferred carbon sources are glucose, sucrose, glucose and sucrose, glucose and xylose and/or glucose, arabinose and xylose. According to one embodiment of the process according to the present invention the assimilable carbon source may be sucrose, glycerin and/or glucose.

The initial concentration of the assimilable carbon source, preferably the initial concentration is, preferably, adjusted to a value in a range of 5 to 250 g/l, preferably 50 to 200 g/l and more preferably 125 to 150 WI, most preferably about 140 g/l and may be maintained in said range during cultivation. The pH of the reaction medium may be controlled by addition of suitable bases as for example, gaseous ammonia, $NH_4OH$, $NH_4HCO_3$, $(NH_4)_2CO_3$, $NaOH$, $Na_2CO_3$, $NaHCO_3$, $KOH$, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, $CaO$, $CH_6N_2O_2$, $C_2H_7N$ and/or mixtures thereof.

Another embodiment of the invention is a process for fermentative production of alanine, pyruvate, succinate, aspartate, malate, lactate, valine and/or leucine, preferably succinate or alanine, more preferably alanine, most preferably L-alanine comprising the steps of I) growing the microorganism according to the invention as defined above in a fermenter and II) recovering alanine, pyruvate, succinate, aspartate, malate, lactate, valine and/or leucine, preferably succinate or alanine, more preferably alanine, most preferably L-alanine from the fermentation broth obtained in I).

The fermentation step I) according to the present invention can, for example, be performed in stirred fermenters, bubble columns and loop reactors. A comprehensive overview of the possible method types including stirrer types and geometric designs can be found in Chmiel: "Bioprozesstechnik: Einführung in die Bioverfahrenstechnik", Volume 1. In the process according to the present invention, typical variants available are the following variants known to those skilled in the art or explained, for example, in Chmiel, Hammes and Bailey: "Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield ($Y_{P/S}$).

Particularly preferred conditions for producing alanine, pyruvate, succinate, aspartate, malate, lactate, valine and/or leucine, preferably succinate or alanine, more preferably alanine, most preferably L-alanine in process step I) are:

Assimilable carbon source: glucose
Temperature: 30 to 45° C.
pH: 6.0 to 7.0
Microaerobic Conditions In process step II) the product is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the fermentation product is further purified. If, however, the fermentation product is converted into a secondary organic product by chemical reactions, a further purification of the fermentation product might, depending on the kind of reaction and the reaction conditions, not necessarily be required. For the purification of the fermentation product obtained in process step II) methods known to the person skilled in the art can be used, as for example crystallization, filtration, electrodialysis and chromatography. The resulting solution may be further purified by means of ion exchange chromatography in order to remove undesired residual ions.

A further embodiment of the invention is a recombinant expression construct comprising a promoter functional in a microorganism operably linked to the nucleic acid as defined in above in (i) to (v). Preferably the promoter is heterologous to the nucleic acid as defined in above in (i) to (v) A further embodiment of the invention is a recombinant vector comprising the nucleic acid molecule as defined above in (i) to (v) or the recombinant expression construct as defined above.

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. it must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as start codon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41$ (% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M Na3PO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M Na3PO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M Na3PO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W, R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in defines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perform gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query defline [TIF]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -l Restrict search of database to list of GI's [String] Optional; -U Use lower case filtering of FASTA sequence [TIF] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO: 1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. The term also comprises nucleic acid molecules which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or -5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the latter being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used inter-changeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, alanine) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant DNA molecule.

The term "recombinant" with respect to DNA refers to DNA molecules produced by man using recombinant DNA techniques. The term comprises DNA molecules which as such do not exist in nature or do not exist in the organism from which the DNA is derived, but are modified, changed, mutated or otherwise manipulated by man. Preferably, a "recombinant DNA molecule" is a non-naturally occurring nucleic acid molecule that differs in sequence from a naturally occurring nucleic acid molecule by at least one nucleic acid. A "recombinant DNA molecule" may also comprise a "recombinant construct" which comprises, preferably operably linked, a sequence of nucleic acid molecules not naturally occurring in that order. Preferred methods for producing said recombinant DNA molecule may comprise cloning techniques, directed or non-directed mutagenesis, gene synthesis or recombination techniques.

An example of such a recombinant DNA is a plasmid into which a heterologous DNA-sequence has been inserted or a gene or promoter which has been mutated compared to gene or promoter from which the recombinant DNA derived. The mutation may be introduced by means of directed mutagenesis technologies known in the art or by random mutagenesis technologies such as chemical, UV light or x-ray mutagenesis or adapted evolution technologies.

The term "adapted evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure (Dragosits, M. & Mattanovich, D. Adaptive laboratory evolution—principles and applications for biotechnology. Microbial cell factories 12, 64, doi:10.1186/1475-2859-12-64 (2013); Zhang, X. et al. Metabolic evolution of energy-conserving pathways for succinate production in *Escherichia coli*. Proceedings of the National Academy of Sciences 106, 20180-20185, doi:10.1073/pnas.0905396106 (2009)).

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, Calif., USA) using the Sanger technology (Sanger et al., 1977). Unless described otherwise, chemicals and reagents are obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases are from New England Biolabs (Ipswich, Mass., USA) or Roche Diagnostics GmbH (Penzberg, Germany). Oligonucleotides are synthesized by Eurofins MWG Operon (Ebersberg, Germany).

Example 1

*E. coli* W (LU17032) was engineered for L-alanine production by inactivation of the ackA-pta, adhE, frdABCD and pflB ORFs and replacement of the ldhA ORF by a codon-optimized variant of the alaD gene (alaD-gstear).

The ackA-pta, adhE, frdABCD and pflB ORFs were inactivated by insertion of an FRT-flanked kanamycin resistance cassette, followed by removal of the antibiotic resistance cassette by FLP recombination.

The ldhA gene was replaced by alaD-gstear and a downstream FRT-flanked zeocin resistance cassette, which was finally removed by FLP recombination.

Materials and Methods
Bacterial Culture

*E. coli* W (LU17032) was cultured in Luria-Bertani (LB) liquid medium or on Luria-Bertani solid medium. Occasionally, clones were passaged over M9 minimal agar containing 10 mM Sucrose to confirm W strain identity. Antibiotics were added to the liquid and solid media as appropriate, to final concentrations of 15 µg/ml (kanamycin, chloramphenicol), 25 µg/ml (zeocin) or 3 µg/ml (tetracyclin).

Red/ET Recombination

Red/ET recombination was performed using standard protocols of Gene Bridges GmbH (www.genebridges.com). Briefly, Red/ET-proficient *E. coli* W was aerobically grown at 30° C. to an OD600 nm of ~0.3. Expression of red genes was induced by adding 50 µl of 10% (w/v) L-arabinose, followed by a temperature increase to 37° C. Arabinose was omitted from uninduced control cultures. After 35 min of incubation at 37° C. the cells were washed twice with ice cold 10% (v/v) glycerol and electroporated with 500 ng of PCR product at 1.35 kV, 10 µF, 600Ω. The cells were then resuspended in 1 ml ice-cold LB medium and aerobically grown at 37° C. for approximately 1.5 h. Cultures were then plated on LB agar containing 15 µg/ml kanamycin (knockouts) or 25 µg/ml zeocin (knockin).

FLP Recombination

Flanking FRT sites allowed removal of antibiotic resistance markers by FLP recombination following modification of the *E. coli* chromosome. FLP recombination leaves a single FRT site (34 bp) as well as short flanking sequences (approx. 20 bp each) which are used as primer binding sites in the amplification of the cassettes.

To perform FLP recombination, plasmid 708-FLPe (Tab. 1) encoding FLP recombinase was introduced into the Red/ET recombinants by electroporation. KanR CmR or ZeoR CmR transformants were used to inoculate 0.2 ml LB cultures, which were incubated at 30° C. for 3 h. FLP activity was then induced by a temperature shift to 37° C., followed by a three-hour incubation at 37° C. Single colonies obtained from these cultures were subsequently screened for a CmS and KanS or ZeoS phenotype.

DNA Preparation and Analysis

*E. coli* genomic DNA (gDNA) was isolated from overnight cultures with the Gentra Pure-gene Yeast/Bact. Kit B (Qiagen, Hilden, Germany). PCR products harbouring knockout or knockin cassettes were amplified from template plasmids with PRECISOR high-fidelity DNA polymerase (BioCat, Heidelberg) and analytical PCR reactions were performed with the PCR Extender System (5PRIME GmbH, Hamburg, Germany), according to the manufacturer's recommendations. PCR amplicons were purified using the GeneJET PCR Purification Kit or the GeneJET Gel Extraction Kit (Fermentas, St. Leon-Rot, Germany) and sequencing was performed by GATC BioTech (Konstanz, Germany) or BioSpring (Frankfurt am Main, Germany).

TABLE 1

Plasmids and primers

| | Relevant characteristics/ oligo sequences (5'→3') | Source |
|---|---|---|
| plasmids | | |
| pRed/ET | red expression plasmid, pSC101-based, Tc$^R$ | Gene Bridges |
| 708-FLPe | FLP recombinase expression plasmid, | Gene Bridges |

TABLE 1-continued

Plasmids and primers pSC101-based, Cm$^R$

| primers (BioSpring) | Sequence | SEQ ID NO |
|---|---|---|
| P395-ackA-pta-check1 | 5'-ACTGCGGTAGTTCTTCACTG-3' | SEQ ID NO: 17 |
| P395-ackA-pta-check2 | 5'-AGTACCTTTCTGGTTTAGCCG-3' | SEQ ID NO: 18 |
| P395-ackA-pta-check3 | 5'-GATAGCAGAAACGGAACCAC-3' | SEQ ID NO: 19 |
| P395-ackA-pta-check4 | 5'-GGTGCTGTTCACACTACCGC-3' | SEQ ID NO: 20 |
| P395-ackA-pta-check5 | 5'-TGACGAGATTACTGCTGCTG-3' | SEQ ID NO: 21 |
| P395-ackA-pta-check6 | 5'-ATTTCCGGTTCAGATATCCGC-3' | SEQ ID NO: 22 |
| P395-adhE-check1 | 5'-GGGTTGACCAGCGCAAATAAC-3' | SEQ ID NO: 23 |
| P395-adhE-check2 | 5'-CAGAAGTGAGTAATCTTGCTTAC-3' | SEQ ID NO: 24 |
| P395-adhE-check3 | 5'-GATCACTTTATCTTCGACGATAC-3' | SEQ ID NO: 25 |
| P395-adhE-check4 | 5'-GCGAACGTGGATAAACTGTCTG-3' | SEQ ID NO: 26 |
| P395-adhE-check5 | 5'-GCTCTTAAGCACCGACGTTGAC-3' | SEQ ID NO: 27 |
| P395-adhE-check6 | 5'-GTCGGCTCATTAACGGCTATTC-3' | SEQ ID NO: 28 |
| P395-frd-check1 | 5'-GACGGATCTCCGCCATAATC-3' | SEQ ID NO: 29 |
| P395-frd-check2 | 5'-TCGCCACCCGCTACTGTATC-3' | SEQ ID NO: 30 |
| P395-frd-check3 | 5'-CAAAGCGTTCTGACGAACCGG-3' | SEQ ID NO: 31 |
| P395-frd-check4 | 5'-TGTGCGATGCACAATATCGTTG-3' | SEQ ID NO: 32 |
| P395-pflB-check1 | 5'-TTGGTTGGGTTGACATACTGG-3' | SEQ ID NO: 33 |
| P395-pflB-check2 | 5'-TGAACTTCATCACTGATAACC-3' | SEQ ID NO: 34 |
| P395-pflB-check3 | 5'-TTCAAAGGAGTGAATGCGACC-3' | SEQ ID NO: 35 |
| P395-pflB-check4 | 5'-GTCGCGGTTATGACAATACAGG-3' | SEQ ID NO: 36 |
| P395-ldhA-check1 | 5'-TACCGTGCCGACGTTCAATAAC-3' | SEQ ID NO: 37 |
| P395-ldhA-check2 | 5'-CATCAGCAGGCTTAGCGCAAC-3' | SEQ ID NO: 38 |
| P395-ldhA-check3 | 5'-ACCTTTACGCGTAATGCGTG-3' | SEQ ID NO: 39 |
| P395-ldhA-check4 | 5'-ACCGTTTACGCTTTCCAGCAC-3' | SEQ ID NO: 40 |
| P395-csc-check1 | 5'-CGAATTATCGATCTCGCTCAAC-3' | SEQ ID NO: 41 |
| P395-csc-check2 | 5'-CGTCTATATTGCTGAAGGTACAG-3' | SEQ ID NO: 42 |
| P395-csc-check3 | 5'-TCGAAGGTCCATTCACGCAAC-3' | SEQ ID NO: 43 |
| P395-csc-check4 | 5'-GATTCCCACCGCAACGTTAG-3' | SEQ ID NO: 44 |

1.1. ackA-Pta Locus—Targeting of ackA-Pta

Approximately 500 ng of the ΔackA-pta PCR construct (1737 bp) were electroporated into Red/ET-proficient E. coli W cells. Eight KanR transformants were analysed for correct integration of the resistance marker cassette by PCR with genome-specific primers. Three clones were subjected to FLP recombination, which was performed as described in Material and Methods (data not shown).

Clone validation. Inactivation of the ackA-pta locus and removal of the kanamycin resistance cassette were confirmed by PCR across the remaining FRT scar. One clone that yielded the correct PCR signal was also confirmed by sequencing.

1.2 adhE Locus—Targeting of adhE

Approximately 500 ng of the ΔadhE PCR construct (1093 bp) were electroporated into Red/ET-proficient E. coli W cells harbouring the ΔackA-pta::FRT modification. Eight KanR transformants were analysed for correct integration of the resistance marker cassette by PCR with genome-specific primers. Two clones were subjected to FLP recombination, which was performed as described in Material and Methods (data not shown).

Clone validation. Inactivation of the adhE locus and removal of the kanamycin resistance cassette were confirmed by PCR across the remaining FRT scar. One clone that yielded the correct PCR signal was also confirmed by sequencing.

1.3 Frd Locus—Targeting of frdABCD

Approximately 500 ng of the ΔfrdABCD PCR construct (1093 bp) were electroporated into Red/ET-proficient E. coli W cells harbouring the ΔackA-pta::FRT and ΔadhE::FRT modifications. Eight KanR transformants were analysed for correct integration of the resistance marker cassette by PCR with genome-specific primers. One clone was subjected to FLP recombination, which was performed as described in material and Methods (data not shown).

Clone validation. Inactivation of the frd locus and removal of the kanamycin resistance cassette were confirmed by PCR across the remaining FRT scar. One clone that yielded the correct PCR signal was also confirmed by sequencing.

1.4 pflB Locus—Targeting of pflB

Approximately 500 ng of the ΔpflB PCR construct (1093 bp) were electroporated into Red/ET-proficient E. coli W cells harbouring the ΔackA-pta::FRT, ΔadhE::FRT and ΔfrdABCD::FRT modifications. Eight KanR transformants were analysed for correct integration of the resistance marker cassette by PCR with genome-specific primers. Four clones were subjected to FLP recombination, which was performed as described in Material and Methods (data not shown).

Clone validation. Inactivation of the pflB locus and removal of the kanamycin resistance cassette were confirmed by PCR across the remaining FRT scar. One clone that yielded the correct PCR signal was also confirmed by sequencing.

1.5 ldhA Locus—Knockin of alaD-Gstear

Approximately 500 ng of the ΔldhA::alaD-gstear PCR construct (1783 bp) were electroporated into Red/ET-proficient E. coli W cells harbouring the ΔackA-pta::FRT, ΔadhE::FRT, ΔfrdABCD::FRT and ΔpflB::FRT modifications. Four ZeoR transformants were analysed for correct integration of the resistance marker cassette by PCR with genome-specific primers. One clone was subjected to FLP recombination, which was performed as described in material and Methods (data not shown).

Clone validation. Integration of alaD-gstear and removal of the zeocin resistance cassette were confirmed by PCR across the remaining FRT scar. One clone that yielded the correct PCR signal was also confirmed by sequencing.

Example 2 HPLC Detection and Quantification of Alanine

The following HPLC method for the alanine detection in the cell culture media was used: Column: Aminex HPX-87C column (Bio-Rad), 300×7.8 mm, i.d. particle size 9 μm
Mobile phase: $Ca(NO_3)_2$ at 0.1 mol/L 90%, Acetonitrile 10%
Flow rate: 0.6 mL/min
Column temperature: 60° C.
Detection: Refractive index detector Under above method, major estimated components in the cell culture sample matrix can be well separated from alanine, without interfering alanine's quantitation.

The amount of the alanine in the sample was determined by external standard calibration method. Standard samples containing alanine from 0.5 to 10.0 g/L were injected and the peak areas were used for calibration. Linear regression coefficient of the calibration curve was 0.9995.

Samples are injected once at 20 μL. Peak areas are used to calculate the amount presenting in the sample by Waters LC Millenium software.

Example 3 HPLC Detection and Quantification of Glucose, Succinate, Lactate, Formate, Acetate and Ethanol HPLC Method Used
Column: Aminex HPX-87H column (Bio-Rad), 300×7.8 mm, i.d. particle size 9 μm
Mobile phase: $H_2SO_4$ 4 mM
Flow rate: 0.4 ml/min
Column temperature: 45° C.
Detection: Refractive index detector The amount of the analytes was determined by external standard calibration method. Standard samples containing glucose from 0.1 to 38.0 g/L, succinate, lactate, formate, acetate and ethanol from 0.05 to 10.0 g/L were injected and the peak areas were used for calibration. Linear regression coefficients for all six calibration curves were better than 0.999.

Samples are injected once at 20 μL. Peak areas are used to calculate the amount presenting in the sample by Waters LC Millenium software.

Example 4: Metabolic Evolution of the E. coli W Stem Derived from Example 1 for Improved Alanine Yield The E. coli stem comprising all mutations as described in Example 1, named E. coli Ex1. was used for a metabolic evolution procedure in order to improve the alanine yield of the E. coli Ex1 stem.

The metabolic evolution was performed as follows: In a first and second evolution round continuous evolution was performed for 500 hours and 750 hours respectively in NBS medium comprising 5% glucose.

NBS Medium:
3.5 g $KH_2PO_4$
5.0 g $K_2HPO_4$
3.5 g $(NH_4)_2HPO_4$
0.25 g $MgSO_4\text{-}7H_2O$
15 mg $CaCL_2\text{-}2H_2O$
0.5 mg Thiamine
1 ml trace metal stock The trace metal stock was prepared in 0.1 M HCL, 1.6 g $FeCL_3\text{-}6H_2O$; 0.2 g $CoCl_2\text{-}6H_2O$; 0.1 g $CuCl_2\text{-}2H_2O$; 0.2 g $ZnCl_2$; 0.2 g $NaMoO_4\text{-}2H_2O$; 0.05 g $H_3BO_3$.

Cells were streaked on LB plates and tested for alanine yield. The best E. coli stem (E. coli Ev1) resulted in fermentation with NBS medium comprising 5% glucose for 24 and 48 h at 37° C. in an alanine yield between 84%-86% compared to the alanine yield of the starting stem E. coli Ex1 resulting in 80%-83%.

E. coli Ev1 was used for further adaptive evolution steps which were performed as batch evolution for 20 days. 5% of the cells were reinoculated in fresh medium every 24 h, 48 h, 72 h and so forth in AM1 medium comprising 14% glucose at 37° C.

AM1 Medium:
19.92 mM $(NH_4)_2HPO_4$=2.6 g IL MW: 132.07
7.56 mM $NH_4H_2PO_4$=0.87 g/L MW: 115
2.0 mM KCl=0.15 g/L MW: 74.55
1.5 mM $MgSO_4\text{-}7H2O$=0.37 g/L MW: 246.5
15 g/L ammonium sulfate was added in the last step
1 mM betain
1 ml trace metal stock
To make 1 L trace metal stock:

The trace metal stock was prepared in 0.12 M HCL, 2.4 g $FeCL_3$-$6H_2O$; 0.3 g $CoCl_2$-$6H_2O$; 0.21 g $CuCl_2$-$2H_2O$; 0.3 g $ZnCl_2$; 0.27 g $NaMoO4$-$2H_2O$; 0.068 g $H_3BO_3$; 0.5 g $MnCl2$-$4H_2O$ From this adaptive evolution the stem *E. coli* Ev2 was isolated. This stem was tested in fermentation which was performed in a fermenter with AM1 medium comprising 14% glucose. The stem *E. coli* Ev2 had an alanine yield between 92%-94% compared to an alanine yield of *E. coli* Ev1 of 91%-92% under same conditions.

After further batch adaptive evolution steps for 300 h in AM1 medium comprising 12% glucose and subsequent 10 batch adaptive evolution steps in the AM1 comprising 12% glucose, the stem *E. coli* Ev3 was isolated.

Testing for alanine yield revealed that the stem *E. coli* Ev3 had an alanine yield between 94%-96% in AM1 medium comprising 12% glucose compared to an alanine yield of *E. coli* Ev2 of 92%-93% under same conditions.

Example 5: Effect of the Increased Expression of the gcvTHP Operon on L-Alanine Productivity An additional copy of the gcvTHP operon (SEQ ID NO: 51) consisting of the ORFs for gcvT (SEQ ID NO: 45), gcvH (SEQ ID NO: 47) and gcvP (SEQ ID NO: 49) was introduced into the pACYC184 plasmid under the control of an IPTG-inducible Ptrc promoter. The vector, designated as pACYC-gcvTHP (SEQ ID NO: 52), was constructed via commercial InFusion cloning technology (Clontech, Mountain View, Calif., USA). The pACYC184 vector (NEB) was linearized with HindIII and SalI restriction endonucleases (NEB). The generated vector backbone was purified by agarose gel extraction. The gcvTHP operon was PCR amplified from wild-type *E. coli* W genomic DNA with primers gcvTHP-pACYC_F (SEQ ID NO: 53) and gcvTHP-pACYC_R (SEQ ID NO: 54). The primers contained additional 15 bp homologous overhangs to the vector backbone and a double-stranded DNA fragment with the Ptrc promoter (SEQ ID NO: 55) that was synthesized by IDT (Integrated DNA Technologies, Inc.). The amplified gcvTHP operon, the upstream Ptrc promoter and the linearized pACYC184 vector backbone were cloned together according to the InFusion cloning manual. The resulting pACYC-gcvTHP plasmid was transformed into *E. coli* strain Ev3 as described in PCT/IB2014/064426 and PCT/IB2014/066686 via electroporation and selected for on LB chloramphenicol plates. Positive constructs were confirmed by DNA sequencing.

The effect of gcvTHP overexpression on L-alanine productivity was tested by comparative cultivation of *E. coli* Ev3 harbouring the empty control plasmid (SEQ ID NO: 56) and *E. coli* Ev3 harbouring the gcvTHP overexpression plasmid pACYC-gcvTHP (SEQ ID NO: 52). Precultures were grown in shake flasks with LB medium supplemented with 25 µg/mL chloramphenicol for plasmid maintenance, 20% filling volume at 37 C and 200 rpm overnight. The fermentation was performed in the DASGIP 1.5 L parallel bioreactor system (Eppendorf) in 500 mL AM 1 medium (2.6 g/L (NH4)2HPO4, 0.87 g/L NH4H2PO4, 0.15 g/L KCl, 0.37 g/L MgSO4.7H2O, 15 g/L (NH4)2SO4, 1 mM betaine, 1 ml/L trace metal stock solution). The trace metal stock comprised 1.6 g/L FeCL3.6H2O; 0.2 g/L CoCl2.6H2O; 0.1 g/L CuCl2.2H2O; 0.2 g/L ZnCl2; 0.2 g/L NaMoO4.2H2O; 0.05 g/L H3BO3, 0.1 M HCL. 140 g/L Glucose were used as carbon source and 25 µg/mL chloramphenicol were added to the fermentation medium to stably maintain the plasmid. Expression of the gcvTHP operon from the Ptrc promoter was induced with 200 µM isopropyl β-D-1-thiogalactopyranoside (IPTG) during exponential growth of cells. Each strain was run in duplicates at 37 C and 400 rpm stirrer speed. 5N NH4OH was used to control the pH to 6.8 and to provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for L-alanine and glucose concentrations.

After 60 h of fermentation time *E. coli* Ev3 in which the gcvTHP operon (SEQ ID NO: 51) was overexpressed from the pACYC-gcvTHP plasmid (SEQ ID NO: 52) reached a significantly higher L-alanine titer of 53.37±1.45 g/L compared to the strain harbouring the empty control plasmid (37.23±0.01 g/L).

We claim:

1. A recombinant microorganism comprising:
   (1) an introduced, increased or enhanced activity and/or expression of a gcvTHP operon, wherein the change in activity is in comparison to a respective reference microorganism without introduced, increased or enhanced activity of a gcvTHP operon, and wherein the gcvTHP operon is selected from the group consisting of:
   (i) a nucleic acid molecule comprising SEQ ID NO: 51,
   (ii) a nucleic acid molecule having at least 80% identity to SEQ ID NO: 51,
   (iii) a nucleic acid molecule encoding each of the polypeptides SEQ ID NO: 46, 48 and 50, and
   (iv) a nucleic acid molecule encoding a polypeptide having at least 60% homology to the polypeptide of SEQ ID NO: 46 and a polypeptide having at least 60% homology to the polypeptide of SEQ ID NO: 48 and a polypeptide at least 60% homology to the polypeptide of SEQ ID NO: 50 and;
   (2) a reduced, repressed or deleted activity and/or expression of an adhE gene, wherein the change in activity is in comparison to a respective reference microorganism without reduced, repressed or deleted activity and/or expression of adhE.

2. The recombinant microorganism of claim 1, further comprising an introduced, increased or enhanced activity and/or expression of an alaD gene wherein the change in activity is in comparison to a respective reference microorganism without introduced, increased or enhanced activity and/or expression of alaD.

3. The recombinant microorganism of claim 1, further comprising a reduced, repressed or deleted activity and/or expression of a pflB gene, wherein the change in activity is in comparison to a respective reference microorganism without reduced, repressed, or deleted activity and/or expression of pflB.

4. The recombinant microorganism of claim 1, further comprising a reduced, repressed or deleted activity and/or expression of a ldhA gene, wherein the change in activity is in comparison to a respective reference microorganism without reduced, repressed, or deleted activity and/or expression of ldhA.

5. The recombinant microorganism of claim 1, further comprising a reduced, repressed or deleted activity and/or expression of a pta gene, wherein the change in activity is in comparison to a respective reference microorganism without reduced, repressed, or deleted activity and/or expression of pta.

6. The recombinant microorganism of claim 1, further comprising a reduced, repressed or deleted activity and/or expression of a frdA gene, wherein the change in activity is in comparison to a respective reference microorganism without reduced, repressed, or deleted activity and/or expression of frdA.

7. The recombinant microorganism of claim 2, wherein the alaD gene is selected from the group consisting of:
(AA) a nucleic acid molecule comprising SEQ ID NO: 15,
(BB) a nucleic acid molecule having at least 80% identity to SEQ ID NO: 15,
(CC) a nucleic acid molecule encoding the polypeptide of SEQ ID NO: 16, and
(DD) a nucleic acid molecule encoding a polypeptide having at least 60% homology to the polypeptide of SEQ ID NO: 16.

8. The recombinant microorganism of claim 3, wherein the pflB gene is selected from the group consisting of:
(A) a nucleic acid molecule comprising SEQ ID NO: 5,
(B) a nucleic acid molecule having at least 80% identity to SEQ ID NO: 5,
(C) a nucleic acid molecule encoding the polypeptide of SEQ ID NO: 6, and
(D) a nucleic acid molecule encoding a polypeptide having at least 60% homology to the polypeptide of SEQ ID NO: 6.

9. The recombinant microorganism of claim 1, wherein the adhE gene is selected from the group consisting of:
(E) a nucleic acid molecule comprising SEQ ID NO: 7,
(F) a nucleic acid molecule having at least 80% identity to SEQ ID NO: 7,
(G) a nucleic acid molecule encoding the polypeptide of SEQ ID NO: 8, and
(H) a nucleic acid molecule encoding a polypeptide having at least 60% homology to the polypeptide of SEQ ID NO: 8.

10. The recombinant microorganism of claim 4, wherein the ldhA gene is selected from the group consisting of:
(I) a nucleic acid molecule comprising SEQ ID NO: 9,
(J) a nucleic acid molecule having at least 80% identity to SEQ ID NO: 9,
(K) a nucleic acid molecule encoding the polypeptide of SEQ ID NO: 10, and
(L) a nucleic acid molecule encoding a polypeptide having at least 60% homology to the polypeptide of SEQ ID NO: 10.

11. The recombinant microorganism of claim 5, wherein the pta gene is selected from the group consisting of:
(M) a nucleic acid molecule comprising SEQ ID NO: 11,
(N) a nucleic acid molecule having at least 80% identity to SEQ ID NO: 11,
(O) a nucleic acid molecule encoding the polypeptide of SEQ ID NO: 12, and
(P) a nucleic acid molecule encoding a polypeptide having at least 60% homology to the polypeptide of SEQ ID NO: 12.

12. The recombinant microorganism of claim 6, wherein the frdA gene is selected from the group consisting of:
(Q) a nucleic acid molecule comprising SEQ ID NO: 13,
(R) a nucleic acid molecule having at least 80% identity to SEQ ID NO: 13,
(S) a nucleic acid molecule encoding the polypeptide of SEQ ID NO: 14, and
(T) a nucleic acid molecule encoding a polypeptide having at least 60% homology to the polypeptide of SEQ ID NO: 14.

13. The recombinant microorganism of claim 1, wherein the microorganism is selected from a genus of the group consisting of *Corynebacterium, Bacillus, Erwinia, Escherichia, Pantoea, Streptomyces, Zymomonas, Rhodococcus*, and *Saccharomyces*.

14. A composition comprising one or more recombinant microorganisms according to claim 1.

15. The composition of claim 14, further comprising a medium and a carbon source.

16. A method for producing a recombinant microorganism with enhanced pyruvate, succinate, aspartate, malate, lactate, valine, leucine and/or alanine yield and/or productivity, which comprises the following steps:
(I) introducing, increasing or enhancing the activity and/or expression of a gcvTHP operon in a microorganism, wherein the change in activity is in comparison to a respective reference microorganism without introduced, increased or enhanced activity of a gcvTHP operon, wherein the gcvTHP operon is selected from the group consisting of:
(i) a nucleic acid molecule comprising SEQ ID NO: 51,
(ii) a nucleic acid molecule having at least 80% identity to SEQ ID NO: 51,
(iii) a nucleic acid molecule encoding each of the polypeptides SEQ ID NO: 46, 48 and 50, and
(iv) a nucleic acid molecule encoding a polypeptide having at least 60% homology to the polypeptide of SEQ ID NO: 46 and a polypeptide having at least 60% homology to the polypeptide of SEQ ID NO: 48 and a polypeptide at least 60% homology to the polypeptide of SEQ ID NO: 50; and
(II) reducing, repressing or deleting activity and/or expression of an adhE gene, wherein the change in activity is in comparison to a respective reference microorganism without reduced, repressed or deleted activity and/or expression of adhE; and
(III) generating a recombinant microorganism with enhanced pyruvate, succinate, aspartate, malate, lactate, valine, leucine and/or alanine yield and/or productivity compared to a respective reference microorganism without reduced, repressed or deleted activity and/or expression of the gcvTHP operon and without reduced, repressed or deleted activity and/or expression of adhE.

17. The method of claim 16, wherein the recombinant microorganism further comprises an increased or enhanced activity and/or expression of an alaD gene, wherein the chance in activity or expression is in comparison to a respective reference microorganism without increased or enhanced activity and/or expression of alaD, and/or a reduced, repressed or deleted activity and/or expression of at least one, at least two, at least three, or all of a pflB gene, an ldhA gene, a pta gene, and an frdA gene, wherein the chance in activity is in comparison to a respective reference microorganism without reduced, repressed or deleted activity and/or expression of pflB, ldhA, pta and/or frdA.

18. The method of claim 16, wherein the microorganism is selected from a genus of the group consisting of *Corynebacterium, Bacillus, Erwinia, Escherichia, Pantoea, Streptomyces, Zymomonas, Rhodococcus*, and *Saccharomyces*.

19. A method of producing pyruvate, succinate, aspartate, malate, lactate, valine, leucine and/or alanine comprising culturing one or more recombinant microorganism according to claim 1 under conditions that allow for the production of pyruvate, succinate, aspartate, malate, lactate, valine, leucine and/or alanine.

20. The method according to claim 19, wherein the microorganism is cultured in a medium comprising between 0.5% and 30% (w/v) of a sugar.

21. The method according to claim 19, wherein the yield of pyruvate, succinate, aspartate, malate, lactate, valine, leucine and/or alanine is at least 80%.

22. The method according to claim 19, wherein the chiral purity of L-alanine is at least 95%.

23. The method according to claim 19, wherein chiral pure L-alanine is produced.

24. A method of culturing or growing a genetically modified microorganism comprising inoculating a culture medium with one or more genetically modified microorganism according to claim 1 and culturing or growing said genetically modified microorganism in culture medium.

25. A process for fermentative production of pyruvate, succinate, aspartate, malate, lactate, valine, leucine and/or alanine comprising the steps of
 I) growing the microorganism according to claim 1 in a fermenter and
 II) recovering pyruvate, succinate, aspartate, malate, lactate, valine, leucine and/or alanine from the fermentation broth obtained in I).

\* \* \* \* \*